(12) United States Patent
Gupta

(10) Patent No.: US 7,908,182 B1
(45) Date of Patent: Mar. 15, 2011

(54) PERSONAL ADVISOR SERVICE AND MECHANISMS FOR ADVICE AND INTERACTIONS

(76) Inventor: Rajiv Gupta, Los Altos, CA (US)

( * ) Notice: Subject to any disclaimer, the term of this patent is extended or adjusted under 35 U.S.C. 154(b) by 1385 days.

(21) Appl. No.: 11/197,907

(22) Filed: Aug. 4, 2005

Related U.S. Application Data

(60) Provisional application No. 60/598,493, filed on Aug. 4, 2004.

(51) Int. Cl.
*G06Q 30/00* (2006.01)

(52) U.S. Cl. .......... 705/26.7; 705/26; 705/27; 705/36 R; 705/39; 705/37; 705/35; 705/43; 705/8; 705/9; 705/1; 705/14; 705/15; 705/16; 705/17; 705/3; 235/375; 235/379; 709/227; 715/207

(58) Field of Classification Search ............ 705/26, 705/27, 36 R, 39, 37, 43, 35, 8, 9, 1, 15, 17, 705/14.16, 14.26, 14.39; 707/1, 3; 709/227; 235/375, 379; 715/207
See application file for complete search history.

(56) References Cited

U.S. PATENT DOCUMENTS

| | | | |
|---|---|---|---|
| 7,130,815 B1 * | 10/2006 | Gupta | 705/26 |
| 7,162,436 B1 * | 1/2007 | Eckel, Jr. | 705/26 |
| 7,212,990 B1 * | 5/2007 | Greden et al. | 705/26 |
| 7,216,092 B1 * | 5/2007 | Weber et al. | 705/26 |
| 2006/0010117 A1 * | 1/2006 | Bonabeau et al. | 707/3 |

OTHER PUBLICATIONS

"Creating user profiles to improve information quality"; Henczel, Sue; May-Jun. 2004, ISSN:0146-5422; extracted from Dialog database on line; 06787898 & supplier No. 116187069.*

* cited by examiner

*Primary Examiner* — Yogesh C Garg
(74) *Attorney, Agent, or Firm* — Faegre & Benson LLP

(57) ABSTRACT

Methods, systems and business models are provided for an effective personal advisor service. According to one embodiment, a personal advisor service performs a method of identifying and notifying a subscriber of the personal advice service of information regarding potential transactions, potential transaction providers, or transactable information determined to address or alleviate a need of the subscriber. First, a computer system of a personal advice service receives information indicative of one or more needs of the subscriber of the advice service. The personal advice service then generates information regarding one or more offers for the subscriber by identifying and selecting among potential transactions, potential transaction providers, or transactable information that are determined to address or alleviate a need of the one or more needs. Finally, the personal advice service causes the one or more offers to be communicated to the subscriber in accordance with a reachability profile established by the subscriber.

19 Claims, 12 Drawing Sheets

- Create personal presence (e.g., web page)
- Add profile information
- Indicate intent to buy specific product or service
- Add constraints/preferences to select between multiple providers
- Connect with recommended provider

- Browse list of profile criteria
- Add reachability criteria
- Request new categories of products or services
- Give feedback, rating, or recommendation
- Request rating
- Ask to connect with someone or some people with specific attributes (make "connect" request)
- Respond to "reach" requests
- Indicate privacy of attributes
- Ask for interests or choices of people with specific criteria ("similar to")
- Request new attributes in profile
- Get statistics of people on system
- Access interaction history

- Register to become provider
- Agree on terms of qualified lead
- Make offer and specify constraints on offer (to specific person, to a set number of qualified people, etc.)
- Enter payment information

- Browse list of profile criteria
- Add reachability criteria
- Request new categories of products or services
- Give feedback, rating, or recommendation
- Request rating
- Ask to connect with someone or some people with specific attributes (make "connect" request)
- Respond to "reach" requests
- Indicate privacy of attributes
- Ask for interests or choices of people with specific criteria ("similar to")
- Request new attributes in profile
- Get statistics of people on system
- Access interaction history

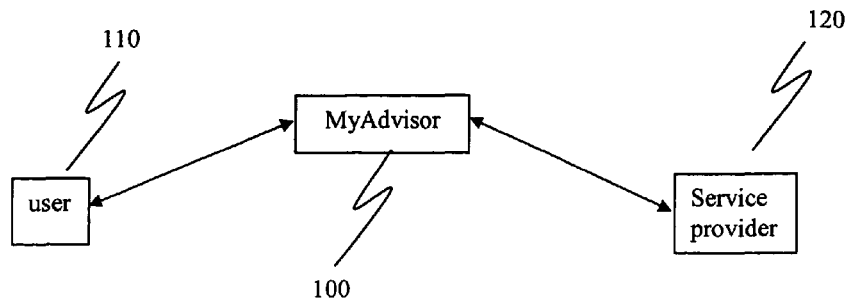

- Create personal presence (e.g., web page)
- Add profile information
- Indicate intent to buy specific product or service
- Add constraints/preferences to select between multiple providers
- Connect with recommended provider

- Browse list of profile criteria
- Add reachability criteria
- Request new categories of products or services
- Give feedback, rating, or recommendation
- Request rating
- Ask to connect with someone or some people with specific attributes (make "connect" request)
- Respond to "reach" requests
- Indicate privacy of attributes
- Ask for interests or choices of people with specific criteria ("similar to")
- Request new attributes in profile
- Get statistics of people on system
- Access interaction history

- Register to become provider
- Agree on terms of qualified lead
- Make offer and specify constraints on offer (to specific person, to a set number of qualified people, etc.)
- Enter payment information

- Browse list of profile criteria
- Add reachability criteria
- Request new categories of products or services
- Give feedback, rating, or recommendation
- Request rating
- Ask to connect with someone or some people with specific attributes (make "connect" request)
- Respond to "reach" requests
- Indicate privacy of attributes
- Ask for interests or choices of people with specific criteria ("similar to")
- Request new attributes in profile
- Get statistics of people on system
- Access interaction history

FIG. 1

PERSONAL ADVISOR SERVICE AND MECHANISMS FOR ADVICE AND INTERACTIONS

This application claims the benefit of Provisional Application No. 60/598,493, filed Aug. 4, 2004, which is hereby incorporated by reference in its entirety for all purposes.

COPYRIGHT NOTICE

Contained herein is material that is subject to copyright protection. The copyright owner has no objection to the facsimile reproduction of the patent disclosure by any person as it appears in the Patent and Trademark Office patent files or records, but otherwise reserves all rights to the copyright whatsoever. Copyright ® 2004-2005, Rajiv Gupta.

BACKGROUND

1. Field

Embodiments of the present invention generally relate to personal advisor services and online or telephone-based services, and in particular to systems and methods for allowing personal information of an end user to be employed while also maintaining privacy to help people run their lives more efficiently by, for example, providing offers, recommendations, giving advice and/or proactively locating and identifying opportunities, such as transactions, providers, products and/or services that may be of interest to the end user, based on expressed and/or unarticulated needs of the end user.

2. Description of the Related Art

The interne has been a great medium to distribute news and information widely. Many companies put their product or service brochures on the internet in the hopes of generating business from the multitudes of people who access the interne. However this plethora of information on the internet is also one of its challenges. Providers of products and services need to find ways in which prospective online buyers can find them through the flood of information on the internet. This need is acute enough that these providers buy keywords on search sites or otherwise buy ads to reach these prospective buyers.

Conversely, prospective buyers have the challenge that they need to filter through the cacophony of all these businesses, very often touting inconsistent criteria, each trying to catch the buyers' attention to find the ones that are most suited to meeting their needs. In the physical world this constant, behind-the-scenes filtering and selecting is one of the most important functions that buyer-side brokers, agents, or advisors fulfill. These advisors, typically focusing on a specific business such as home mortgages, take it upon themselves to track the various sellers of products and services in that specific business.

Another challenge that prospective buyers, both online and offline, face has to do with timing. They have to track the most appropriate time to look for the most appropriate sellers of products and services. So for example a user needs to know that mortgage rates are lower than what he is currently paying. This converts him to a prospective buyer who with this knowledge starts his search for the most appropriate mortgage. Very often the timing and choice of provider are related making the problem more complex for the poor user. So for example it is possible that the mortgage rates quoted to him from different companies are spread over his current mortgage rate. So the question, "are mortgage rates lower than what I am currently paying" translates to the more complex question, "is there a mortgage provider who is quoting lower rates than what I am currently paying".

Some of the best advisors are not only experts in a particular industry and track sellers of products and services in that industry but they also do that as an ever-watchful surrogate of their customer and within the context of their customer's specific situation. The value to users is peace of mind that there is an expert who is constantly watching out for their interests. In the example above, users do not have to worry about tracking mortgage rate trends and they do not have to worry about tracking the offers from multiple providers. For any given risk profile, their mortgage rates will be as good as their advisor.

The users have to disclose information to their advisors so that the advisors can track the industry on their behalf. The advisors have to be paid for their services, very often from the users and sometimes from the service providers with whom the user completes a transaction, for example with whom the user refinances their mortgage.

By sharing information with the advisor, the user is making possible the expression of an unarticulated need. This unarticulated need is a function of the user's state at any point juxtaposed against a changing world. In the example above, the need to refinance may be an unarticulated need. When the advisor has the user's personal information, such as the user's current mortgage rate, the advisor can take the user's articulated or unarticulated need (to refinance), compare the user's current mortgage rate to the mortgage rates at any point, and whenever mortgage rates dip below the user's then current rate, the advisor can create a refinance opportunity that is good for the user, good for the advisor, and good for the lending financial institution. The constant tracking and comparing results in improvements in the user's state, and in this case may result in multiple refinance events, certainly more so than if the user took the onus of tracking multiple mortgage providers and their changing rates.

Another challenge that prospective transaction providers (e.g., prospective product or service providers) face is distinguishing between online users simply looking for information and online users that are interested in buying something. In general, the second type of online user is of more interest to businesses; however, at present both types of online users are generally treated the same.

SUMMARY

Methods, systems and business models are described for an effective personal advisor service. According to one embodiment, a personal advisor service performs a method of identifying and notifying a subscriber of the personal advice service of information regarding potential transactions, potential transaction providers, or transactable information determined to address or alleviate a need of the subscriber. First, a computer system of a personal advice service receives information indicative of one or more needs of the subscriber of the advice service. The personal advice service then generates information regarding one or more offers for the subscriber by identifying and selecting among potential transactions, potential transaction providers, or transactable information that are determined to address or alleviate a need of the one or more needs. Finally, the personal advice service causes the one or more offers to be communicated to the subscriber in accordance with a reachability profile established by the subscriber.

Other features of embodiments of the present invention will be apparent from the accompanying drawings and from the detailed description that follows.

BRIEF DESCRIPTION OF THE DRAWINGS

Embodiments of the present invention are illustrated by way of example, and not by way of limitation, in the figures of the accompanying drawings and in which like reference numerals refer to similar elements and in which:

FIG. 1 is a block diagram conceptually illustrating various interactions among an online advisor service, a user and a service provider in accordance with one embodiment of the present invention.

DETAILED DESCRIPTION

Figure 2:
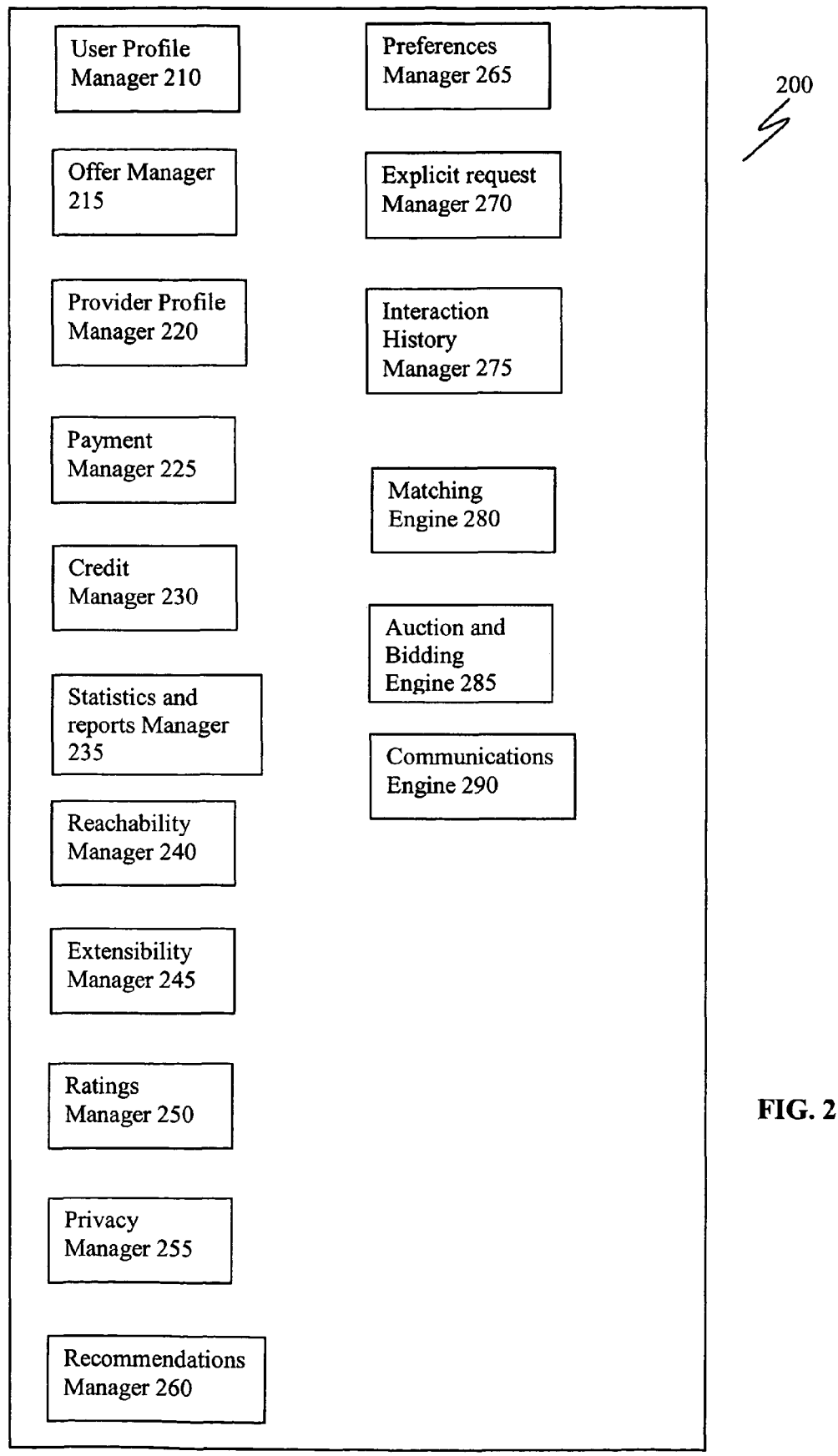
FIG. 2 is a software architecture block diagram conceptually illustrating application-level software components of the online advisor service system in accordance with one embodiment of the present invention.

Methods, systems and business models are described for an effective online advisor service. According to one embodiment, initial interactions by a user with the online advisor service may involve the user navigating to the online advisor service web site, registering or otherwise authenticating himself and logging in. Specific examples of a particular online advice service are referred to herein as the "myadvisor online advisor service," the "myadvisor online advice service," or the "myadvisor service." For convenience, the phrases "myadvisor" and "advisor" are used interchangeably in some contexts.

Importantly, although various embodiments of the myadvisor service are discussed as if the service were implemented at a centralized web location, it is contemplated that such an online advisor service may be centralized or distributed. For example, the myadvisor service may be provided as a distributed service which collects user information, for example, from the users' blogs, from their personal computers, etc.

In any event, once registered, the user may then be provided access to one or more of the functions that the Myadvisor™ web site provides (MYADVISOR™ is a trademark of Rajiv Gupta, the assignee of the present invention). For example, the registered user may (1) enter or change his profile information; (2) enter or change his proactive notification information; (3) choose to interact with one or more of the product or service providers or other users, either those recommended by the advisor or not, either anonymously or not; (4) recommend products or services or categories in one or more categories; (5) rate one or more service providers that he has had experience with; etc.

The profile information may be used by the myadvisor service to help optimize various categories or aspects of the user's life by proactively seeking out opportunities for the user relating to expressed needs or desires indicated within the profile information, inferred needs or desires deduced based at least in part on information within the profile, and/or unarticulated and potentially unperceived opportunities inferred or otherwise derived based at least in part on the profile information. For example, expressed needs may include the user indicating something like "I would like to buy a digital camera, not more than 2 years old, at least 4 megapixels, from Sony or Fuji" in his profile, and responsive thereto the myadvisor service tries to find some provider (or other user) interested in selling such a digital camera to the user. Identifying opportunities regarding inferred needs may involve the user simply providing an indication about the type of home he owns, the type of home owners' insurance and/or information about his mortgage balance and rate, in which case the myadvisor service may attempt to find a better insurance rate, an equivalent insurance rate with more coverage, and/or a better mortgage for the user. As an example of proactively addressing unarticulated needs, the myadvisor service may also find a possible buyer for the user's home even though the user had not thought of selling his home. In one embodiment, the myadvisor service may also allow providers to create profiles as mentioned above for the case of users and may also proactively identify opportunities for providers in a similar manner. In one embodiment, the subscriber may associate with an expressed need a deadline by which he needs to receive information, thereby encouraging feedback from providers within an appropriate timeframe.

In the following description, numerous specific details are set forth in order to provide a thorough understanding of embodiments of the present invention. It will be apparent, however, to one skilled in the art that embodiments of the present invention may be practiced without some of these specific details. In other instances, well-known structures and devices are shown in block diagram form.

Embodiments of the present invention include various steps, which will be described below. The steps may be performed by hardware components or may be embodied in machine-executable instructions, which may be used to cause a general-purpose or special-purpose processor programmed with the instructions to perform the steps. Alternatively, the steps may be performed by a combination of hardware, software, firmware and/or by human operators.

Embodiments of the present invention may be provided as a computer program product, which may include a machine-readable medium having stored thereon instructions, which may be used to program a computer (or other electronic devices) to perform a process. The machine-readable medium may include, but is not limited to, floppy diskettes, optical disks, compact disc read-only memories (CD-ROMs), and magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments of the present invention may also be downloaded as a computer program product, wherein the program may be transferred from a remote computer to a requesting computer by way of data signals embodied in a carrier wave or other propagation medium via a communication link (e.g., a modem or network connection).

While for sake of illustration embodiments of the present invention are described from the perspective of an end user which is typically a consumer of goods or services, the methods and systems of the present invention are equally applicable to users that are providers of goods or services. For example, the user may actually end up selling and the "service or product provider" may actually do the buying. So, consider the case where the user indicates an interest in selling his 1996 Mercury Sable, or the case that the user mentions in his profile that he has the car, the myadvisor service advises him that there is a buyer for the car and the user decides to sell. In this case, the user is the seller and the provider (which might be a used-car company or another user) could be the buyer.

Additionally, in accordance with various aspects of the present invention described further below, the exact symmetric case where user is replaced by provider and provider is replaced by user is also contemplated and addressed by various embodiments of the myadvisor service. So, for example, where user privacy is discussed, so is provider privacy. Similarly when non-intrusive communication with the user is being described, so is the non-invasive communication with the provider. And so on. Once the service has all this information about the user, it can help provide much better search results. So for example if the user makes the advisor page his home page and launches his searches from there, then the advisor can enhance the search query with selective information from the user's profile, or from those of other "similar" users. As an example of profile-based search consider the user whose profile suggests that he has a home in Los Altos, Calif. and his mortgage is $1M. Now when he searches for "mortgage providers" the providers that cater to that type of mortgage will appear higher in the search results. Similarly, if from the user's profile and others with similar profiles it is inferred that he prefers high-end cars, then when he searches for "jaguar" he will first be presented with results that match the luxury car.

Finally, while for convenience embodiments of the present invention are described in the context of an online advisor service, it should be recognized that various features described herein are equally applicable to telephone-based interactions. For example, subscribers to a personal advisor service employing telephone-based interactions may employ interactive voice response (IVR) systems, also known as voice response and automated voice response systems. Furthermore, various features described herein have broad applicability outside the context of providing advice. For example, the managed-intrusive communication methodologies may be applied to other services and web sites which interact with the user and want to give the user the control of reachability. Another example is creating a market out of what the user wants to buy (as opposed to what the user wants to sell as in eBay). Yet another example is creating markets out of unstated intentions, where the user has not indicated an interest to sell but is informed of the prices and possibly even of bids to encourage him to sell. Yet another example is making available other user's choices without violating privacy. This ability to look at the choices of other users of a particular type, almost like a social recommendation or community sensitivity, is useful in many other types of services. For example, in the context of searching where a search engine can use the fact that others in a particular demographic or community chose one type of result for a term over another may be useful in making search results more useful to users of search engines more often. And so on.

Terminology

Brief definitions of terms used throughout this application are given below.

The terms "connected" or "coupled" and related terms are used in an operational sense and are not necessarily limited to a direct connection or coupling.

The phrases "in one embodiment," "according to one embodiment," and the like generally mean the particular feature, structure, or characteristic following the phrase is included in at least one embodiment of the present invention, and may be included in more than one embodiment of the present invention. Importantly, such phrases do not necessarily refer to the same embodiment.

If the specification states a component or feature "may", "can", "could", or "might" be included or have a characteristic, that particular component or feature is not required to be included or have the characteristic.

The term "need" generally relates to something (tangible or intangible) that is wanted or required to increase a person's quality of life, general wellbeing or happiness. Consequently, as used herein, a need is intended to broadly encompass anything along the continuum of things (e.g., products or services) that people believe they must have to those things that are merely desired or wanted, but which are more discretionary. Examples of needs therefore include, but are not limited to, consumer goods and services, information regarding potential transactions that may be of benefit, information regarding potential transaction providers that may be of interest to the subscriber, transactable information, maximum utility (measured in terms of a payoff function or the happiness or satisfaction gained from a good or service), efficiency, privacy, respect, safety, comfort, and the like. According to various embodiments of the present invention, an online advice service acts as an automated agent on behalf of subscribers to proactively identify opportunities to meet perceived needs of subscribers. For example, the online advice service may identify and then suggest or bring to the attention of a subscriber transactions that are determined to maximize anticipated payoff for the subscriber or at least better the subscriber's current status or situation in some measurable way. In one embodiment, the subscriber may set a configurable threshold of improvement that must be achieved before a recommendation will be made or offer communicated by the myadvisor service. For example, it may not be worth a particular subscriber's time or effort to refinance their mortgage to simply achieve a 0.25% reduction their rate. Consequently, a subscriber may wish to mask alerts that do not achieve at least a $X/month reduction in payments or a X percent decrease in their effective annual percentage rate, for example. The configurable parameter may be a global parameter or may be set on a need-by-need basis. Alternatively, such a threshold parameter might be available after a first recommendation/suggestion/offer is made by the myadvisor service, thereby allowing the subscriber to "set a bar" for subsequent recommendations/suggestions/offers of a particular type or in general inform or teach the myadvisor service of the user's preferences, further profile details, or selection criteria. In another embodiment, a "more like this" option may be provided to a subscriber along with recommendations/suggestions/offers made by the myadvisor service, thereby allowing the myadvisor service to "learn" about the type of recommendations/suggestions/offers that are most valued by the subscriber.

The term "offer" generally refers to not only to an offer in the contract sense, but additionally to a product or service offering of a provider, a recommendation or suggestion relating to a product or service offering of a provider, information regarding a potential transaction, information and/or contact information regarding a potential transaction provider, transactable information, or other information that may be of interest to a subscriber, including, but not limited to news bulletins, recalls, side effects, breaking news, etc.

The phrases "online advisory service" or "online advice service" generally refers to a resource that provides advice and that is accessible via a public or private network, the telephone, the Internet, an Intranet, an Internet Service Provider (ISP), a remote computer, an electronic database, or the like.

The term "profile" generally refers to information, state, and explicit or implicit requests/desires of the user in multiple categories—possessions, interests, health, family, work, education, finances, community, etc.—with each category having multiple recursive sub-categories and each sub-category having a set of multiple attributes. So for example the category "possessions" may have sub-category "house" which may have attributes, "owned/rented/leased", "address", "size", etc.

The phrase "reachability profile" generally refers to information used by an online advisor service to determine if, when, and how the service should communicate recommendations or particular types or categories of recommendations to a subscriber of the online advisor service. For example, a reachability profile may be used by a subscriber to configure proactive notifications by the online advisor service with respect to new providers, transactions, or information that might be of interest to the subscriber. The reachability profile may also be used by the online advisor service to determine the format and/or level of detail of recommendations. For example, based on the reachability profile, the online advisor service may (1) provide a synopsis of information relating to, underlying or forming the basis for a recommendation; (2) provide the information in its original form; or (3) provide a hyperlink to the information. Further, the reachability profile may specify certain information should be communicated to the subscriber via the subscriber's home page at the online advice service web site, phone, fax, short message service (SMS), pager, instant messaging (IM), email, or other current or future means of communication. According to one embodiment, an online advisor service, may provide the subscriber with default options and helpful hints on appropriate frequency of proactive notification. In one embodiment, the online advisor service may also inform the subscriber of notification choices that are commonly made by other subscribers, or how frequently a particular piece of information is likely to change or has historically changed. Depending upon the particular embodiment, the reachability profile may be independent of the subscriber's profile or may be a subset of the information provided within the subscriber's profile.

The term "responsive" includes completely or partially responsive.

Overview

One or more embodiments of the present invention may include combinations of various of the following features:

1. Transaction providers are provided with the ability to search adhoc comments posted by end users to facilitate identification of potential transaction opportunities.
2. A channel that guarantees and respects privacy while allowing very private information to be used to help people run their lives more efficiently.
3. Provision of customer surrogate services.
4. Provision of provider surrogate services.
5. Mechanisms to facilitate non-intrusive, managed-intrusion communication.
6. Methods of choosing the best offer and/or transaction provider.
7. Methods of choosing the best user.
8. An online advisor service which is free to the users/buyers and charges service or product providers a finder's fee, bounty, or placement fee to connect them to interested, highly qualified users.
9. Using a subscriber's personal information to create an ad hoc market.
10. Using the subscriber's personal information to create a market where the subscriber may become a seller.
11. Assisting a subscriber in making a decision by presenting information regarding choices made by other subscribers and/or decision-making criteria employed by other subscribers without violating the privacy of such other subscribers.
12. Subscribers as service recommenders—harnessing the collective knowledge and experience of the myadvisor service subscribers to be informed of deals that may not have otherwise been found and which can be used for the benefit of other subscribers.
13. Connecting with providers by soliciting feedback and contributions from experts.
14. Publishing an anonymous aggregate summary of subscriber needs to service providers to enable them to make a bid for the subscribers' business.
15. Generating revenue by allowing existing and prospective providers to query aggregate user profiles without violating user privacy.
16. Tracking service provider ratings and maintaining a service provider rating system based on feedback provided by subscribers that have interacted with service providers.
17. Tracking subscriber ratings and maintaining a subscriber rating system based on feedback received from providers that have interacted with subscribers.
18. Dynamic evolution of buyer-seller ontology.
19. Enabling anonymous interaction between profiled participants.

According to one embodiment of the present invention, transaction providers (e.g., product and/or service providers) may search adhoc comments posted by end users. For example, a user of the myadvisor web site may post a comment indicating he is looking for a car, e.g., an Acura LX newer than 2000. In one embodiment, the myadvisor service allows car dealers to search for people interested in their products/services and pay for the referral. In one embodiment, the transaction provider is also provided with the ability (via manual intervention or otherwise) to help the user navigate, refine searches, evaluate alternatives, etc., with the hope of influencing their buying decision.

In one embodiment, at the time the user posts his question, comment, interest, need or request for information, the user may provide a username and password for a personal results web page where he can later pick up the result(s). The user may also provide preference information regarding proactive notification. For example, the user may indicate he wants to be notified when the results are available. Alternatively, the user may indicate he is willing to log into the myadvisor web site to obtain the result(s). In any event, after the user has posted the question, comment, interest, need or request for information, the myadvisor service then may make that information available to all subscribing providers—businesses, consultants, advisors, etc—without disclosing the identity of the user to the providers. These providers may then use whatever tools they want, for example search for keywords in the posted questions to find the questions that they are interested in or to find answers to the questions on behalf of the users.

In one embodiment, the myadvisor service offers to connect these providers to the user and puts a link to the providers with whatever 1 or 2 liner they want to specify on the user's personal home page to attract the user's eye. According to one embodiment, if the user clicks on the provider's response and is transported to the phone or web page of the provider, the myadvisor service is due a referral fee, such as a pay-per-click type of fee. Depending upon the implementation, ratings and other features described below may be added to the above for improved interactions.

According to one embodiment of the present invention, a channel is built that guarantees and respects privacy of online service subscribers while allowing very private information to be used by the online advice service to help people run their lives more efficiently. For example, a subscriber may enter very personal or private information at the myadvisor web site. The myadvisor service may then anonymize the identity of the subscriber and may use the information to proactively find all providers or products (including services) that may be of interest to the subscriber. In one embodiment, the user's information is entered into a database. New data, such as the new mortgage rates that lending institutions publish on a daily basis, may be compared to the mortgage rates of all users in the system. Any users whose existing mortgage rates are higher than the new ones may then be identified as prospects for notification. Due to the anonymization the providers cannot identify and directly contact the prospects. Moreover, in the general case, the subscriber has entered personal information on his personal page at the myadvisor site and since it is only the subscriber who accesses his personal page through say a username and password, their identity is not disclosed to any other subscriber, user or provider. In fact, even the myadvisor service may not need to uniquely identify the subscriber. This protects the subscriber's privacy, prevents them from being barraged with offers, and it protects the intermediary status of the myadvisor service.

In one embodiment of the present invention, a customer surrogate service is provided. For example, the subscriber may maintain his profile with the myadvisor service which constantly checks the on-line and off-line world for transactions and/or information that could help the subscriber in one of many categories. The subscriber may not even know that they should be looking for something and may not have indicated specific interest (an unarticulated need). The subscriber can of course mention his need explicitly too. The subscriber does not need to check web sites or proactively search for providers, transactions, or information that could help the user lead a better life. The myadvisor service converts the "fact" in the subscriber's personal information into potential interest that could turn into transactions that bring value to the subscriber, to the provider, and to the myadvisor service. The myadvisor service may do this on behalf of subscribers in multiple categories, constantly, and comprehensively, while maintaining the privacy of the subscribers (like a surrogate, proxy, or really good personal assistant).

In accordance with one embodiment, mechanisms are provided to facilitate non-intrusive, managed-intrusion communication. Just as the subscriber does not wish to be barraged by offers from different providers of products or services in which the subscriber may have an interest, so does the subscriber not want to be barraged by the myadvisor service. In one embodiment, the subscriber is informed of possible transactions and providers that might be of interest him when he visits his personal home page at the myadvisor service web site. The myadvisor service also allows the subscriber to specify his "reachability" profile. This profile specifies if, when and how the myadvisor service should proactively notify the subscriber of new providers, transactions, or information that might be of interest to the subscriber, whether the information or a synopsis of the information should be sent or a hyperlink to the information or a hyperlink to the user's home page at the myadvisor service web site should be sent, etc. So, for example, the subscriber may specify that any new information related to possible side-effects of a drug that the subscriber is taking should be sent as an SMS and IM, any new provider of a better mortgage rate should be sent as email, etc. The myadvisor service may also provide the subscriber with default options and helpful hints on appropriate frequency of proactive notification. In one embodiment, the myadvisor service may also inform the subscribers of notification choices that are commonly made by other subscribers, or how frequently a particular piece of information is likely to change or has historically changed.

In one embodiment of the present invention, methods of choosing the best offer and/or transaction provider are provided by including a number of criteria, including, but not limited to, best deal for the subscriber/customer (which itself may have multiple dimensions, some of these are explicitly characterized and presented to the subscriber, for example, the lowest rate for an adjustable, no points mortgage may be one dimension and the lowest rate for a 30-year fixed, no points mortgage may be another; others may be implicit with a pointer to more information for the discerning subscriber), best reputation amongst providers, best fees for the myadvisor service, etc. In one embodiment, providers are sought and prioritized based on the subscriber's profile (in some cases the profile may have to be iteratively refilled in order to select the best provider(s)), so for example only providers who are offering interest rates lower than the subscriber's current rate may be considered. In one embodiment, the subscriber may indicate his preferences, e.g., particular provider, or BBB rating of provider, or find cheapest, and the myadvisor service finds the best provider that meets those preferences. The subscriber may need to do no more research and would be able to transact with the recommended provider. In another possible embodiment, the myadvisor service may also recommend certain criteria that might be useful for the user to think about or consider, perhaps based on what other "similar" subscribers or similarly situated subscribers care about or based on decisions made by "similar" subscribers or similarly situated subscribers, perhaps based on the "best practice" recommendations from the myadvisor service itself, etc.

According to one embodiment, an online advisor service is provided without charge to subscribers that are users/buyers and charges subscribers that are service or product providers a finder's fee, bounty, or placement fee to connect them to interested, highly qualified potential buyers. One of the ways for the myadvisor service to make money is to charge service providers a fee for every transaction (or introduction) enabled through the myadvisor service. This transaction may be a subscriber making a purchase from a provider or simply requesting more information which may manifest in many different ways, for example a click-through to the provider's web site, a call-through to the provider's phone or call center, etc. Another example of how the myadvisor service may make money is to charge the providers placement fees to simply be put in front of the user, even if the user were not to select that particular provider.

One advantage to the service provider in this context is reduced customer acquisition costs in getting to a highly qualified customer. An advantage to the subscriber/customer is that he gets a very valuable personal assistant/advisor service for free. More subscribers and users, leads to more prospective buyers, which leads to service providers who want to make sure they get a chance to reach the mass of users, which further leads to self-registration and therefore lower cost of sales of getting service provider information that can be compared and presented to the subscriber base; and more service providers leads to more competition, which leads to better service and prices (and potentially better margins to the myadvisor service), and which further leads to more subscribers and users.

As an illustration of a sample subscriber scenario, the subscriber may simply provide some factual information about himself in his profile, for example that his current mortgage rate is 6.5%. The subscriber may also provide information about a particular product of interest, e.g., interested in buying digital camera, 4 mega pixels, from one of Sony, Fuji, or Olympus. In one embodiment, the myadvisor service creates a bidding process from service and product providers to address the subscriber's needs. In another embodiment, the myadvisor service lets the subscriber know of the current best price being quoted for items or services of interest. According to one embodiment, the myadvisor service makes public the best offer being quoted by service and product providers so that other service and product providers choose to compete and offer lower prices, all to the benefit of the subscribers/prospective customers. In another embodiment, the price is not made public so that providers put in their absolute best offer instead of one which is only incrementally better than others. The embodiments described above are simply examples. In general, any auction or bidding algorithm and process can be applied to this unique form of prospective buyer and seller/provider interaction and are all intended to be encompassed by this disclosure.

According to one embodiment of the present invention, subscribers' personal information may be used to create an ad hoc market where the subscriber may be a seller. The subscriber may enter information about himself in many categories, for example current mortgage, current description of house, prescriptions, cars, other possessions, etc. The myadvisor service can then help the subscriber track news or information related to his situation, for example, a side-effect of nausea has been reported for people over 50 taking more than 2 acetaminophens a day. The myadvisor service can also help the subscriber track news or information related to his possessions. For example, a subscriber may be notified by the myadvisor service of the fact that a factory recall has been issued on 1996 Mercury Sables. One such piece of information can be the potential "market value" of the possession, for example, a 1996 Mercury Sable has a market value of $4000-$4500. This may induce a subscriber to sell his possession, something he may not have even considered before being made aware of the market value and/or the existence of a prospective purchaser. The myadvisor service may obtain a listing or transaction fee if responsive to the notification the subscriber does decide to sell his possession. In this case, the terms buyer and seller are potentially reversed. This notion of a subscriber or user or business as seller and another subscriber or user or business as buyer is applicable to other embodiments described herein as well.

In one embodiment of the present invention, the myadvisor service may assist a subscriber in making a decision by presenting information regarding choices made by other subscribers and/or decision-making criteria employed by other subscribers without violating the privacy of such other subscribers. Subscribers are best served by a personal advisor who studiously, without conflict of interest, and with singular focus looks after the subscriber's interest and presents the subscriber with recommendations in the subscriber's best interests. In the case of complex services, the myadvisor service may also recommend particular evaluation criteria that the subscriber should consider in connection with selecting the "best" provider. For example, if multiple lending institutions offer the same low mortgage rate, the myadvisor service may recommend that the subscriber consider the larger by assets or older of the multiple lending institutions. However, some criteria may be less easy to recommend, or the user may be interested to know what choices others have made—both the provider that other users selected and/or the criteria they used. According to one embodiment, the myadvisor service allows subscribers to explicitly share their choices with select groups of other subscribers by, for example, designating their sharing preferences as share with all, share with a list of friends, share without disclosing identity, etc. Conversely, subscribers may be interested in looking at the choices of other users within some constraints, presumably but not restricted to others "like me" or "like them". The myadvisor service allows users to select criteria of who to disclose their choices to. The myadvisor service may also allow subscribers to select criteria of other subscribers whose choice of provider or of selection criteria they are interested in knowing. In this case, the myadvisor service complies with the sharing, confidentiality and/or anonymity preferences of the subscribers meeting the selection criteria before sharing their choices, the criteria they used in making their decisions, etc. Similarly, on the converse side, subscribers may be interested to know who or what types of users are interested in their choices. The myadvisor service similarly obeys the sharing, confidentiality and/or anonymity preferences in making such information available to other users.

According to one embodiment, the myadvisor service, using a host of manual, semi-automated, and automated means, tracks all possible service providers all the time to look for information or transactions that may be of interest to subscribers of the service. The myadvisor service may also harness the collective knowledge and experience of its subscribers to be informed of deals that it may not have found itself and which it can use for the benefit of other subscribers. For example, subscribers may make recommendations of providers to the myadvisor service. In one embodiment, when a recommending subscriber makes a recommendation to the myadvisor service, the recommended provider is placed in a bucket of providers relevant to a particular type of offer. The recommendation bubbles to the top and is further recommended to other users or not based on its merit relative to other providers. In one embodiment, the recommendations of other subscribers may be published separately and shared even if they do not bubble to the top when compared to other providers. In order to encourage subscribers to recommend new providers, the myadvisor service may reward the recommending subscriber. For example, if the recommended provider is selected by another subscriber and a transaction between the recommended provider and the other subscriber is completed, the recommending subscriber may be awarded a coupon, discount, gift card or the like that may be honored by one or more providers that are subscribers to the myadvisor service. In one possible embodiment, some generic profile information of the recommending subscriber may be stored with the recommendation (if so approved by the recommending subscriber) so that other subscribers may view and evaluate what type of subscriber made the recommendation.

According to one embodiment of the present invention, the myadvisor service maintains an internal information model for subscribers, users, providers, and for most types of service or product offers that are of potential interest to subscribers/users. For some services and products, especially for those recently introduced by subscribers or providers or for which the myadvisor service does not have sufficient numbers of registered providers, the information may be more ad hoc. Once there is a more form a information model, the myadvisor service may publish it on its provider site for other providers to view and publish their offers consistent with the model in a self-registration, self-help manner. In order to augment its efforts in standardizing the information models, the myadvisor service may also solicit feedback and contributions from users/experts who visit a special site where all or some information models are displayed, for example those that are not yet standardized. In one embodiment, the myadvisor service rewards users/experts for their contributed information models if they are selected.

In one embodiment of the present invention, an anonymous aggregate summary of subscriber needs may be published to service providers to enable them to make a bid for the subscribers' business. There are many other ways in which the myadvisor service may interact with providers to help them make more aggressive offers to the myadvisor service subscribers/users. For example, the myadvisor service may inform providers of the size of business in a particular sector and/or geographic region, for example the total number of subscribers (as an anonymous aggregate) who are candidates for a type of offer. For example, the myadvisor service may inform the providers that there are 5,000 subscribers with jumbo loans whose mortgages are greater than 6.5%. Consequently, a mortgage provider may choose to offer a lower mortgage rate to each of the 5,000 subscribers with the hope of earning the refinancing business of a larger pool of customers. In one possible implementation, the myadvisor service may let the providers bid for chunks of business. In the previous example of 5,000 subscribers with greater than 6.5% mortgage rates, a mortgage provider may choose to bid to be presented to a subset (e.g., 2,000) of the 5,000 subscribers. In various embodiments, the myadvisor service may then apply one of a number of auctioning and/or batch auctioning algorithms to decide which provider should be presented to how many users, whether the providers are allowed to know of each other's bid or if the bids will be sealed, etc.

According to one embodiment, the myadvisor service may generate revenue by allowing existing and prospective providers to query aggregate subscriber profiles without violating user privacy. There are many ways the myadvisor service can make revenue. Some revenue models were mentioned earlier, such as transaction, placement, or introduction fees from the providers of products or services. In cases where the subscriber/user is a seller, then the myadvisor service may charge the user a fee to sell or it may tack on a fee on top of the user's selling price and therefore in fact get revenue from the buyer. The myadvisor service may also or alternatively make revenue by allowing providers to query aggregate user profiles in such a way that it does not violate the privacy of the users and it does not allow the provider to reasonably accurately identify a particular or a small set of subscribers.

One possible value of providing the ability to perform such a query is that armed with user information providers can create new products. This is thought to potentially be a very useful way to survey the market or determine user demographic information. The provider not only is able to obtain detailed user information (even though anonymized) in multiple categories to create a new product but also has a ready-made channel to get to these users. For purposes of illustration, an example of a new "product" that a provider may choose to create is a singles day at the beach for people with an interest in beach volleyball and ultimate Frisbee in Los Angeles. Another example might be a children's education fund for people with household incomes between $80,000 and $100,000 with 2 kids in the ages of 2-6. Without the help of the aggregate user profile information from the myadvisor service, the provider may not have been able to efficiently determine the fact that there are 20,000 people who meet that demographic. Furthermore, without the myadvisor service as a communication platform, the provider may not otherwise have had a convenient way to reach these people to introduce the new product offer to them. In one possible implementation, as part of the querying process, the myadvisor service keeps track of the exact subscribers whose aggregates are being presented to the providers. As the provider slices and dices the profile database of the myadvisor service and the number of users in the aggregate fall below a particular level, the provider may be prohibited from subsetting that aggregate further. In another embodiment, the myadvisor service tracks all the users who have been in any and all aggregates presented to a provider. Any query that reduces the intersection below a particular threshold may not be permitted—thus solving the problem of a provider attempting to isolate and uniquely identify a user by making many seemingly unrelated queries the intersection of which leads the provider to the particular user.

In one embodiment of the present invention, the myadvisor service maintains a service provider rating system based on feedback provided by subscribers that have interacted with service providers. The myadvisor service may employ many criteria to determine which provider's offer should be made to a subscriber, or which providers' offers should be made to the subscriber, and if multiple providers are to be presented then the myadvisor service may determine in which order they should be presented (especially where the order in which they are presented may imply recommendation or approval by the myadvisor service). One criteria that may be employed is the ratings of the provider from external sources like the Better Business Bureau. Another source of sorting criteria is the ratings, opinions, experiences, and recommendations of the subscribers of the myadvisor service. The myadvisor service may also desire to avoid situations in which providers make aggressive offers to get an introduction to a prospective customer but then either fail to deliver on the offer made or provide poor service. In one embodiment, after a provider is introduced to a subscriber, the subscriber is prompted to rate his experience with the provider which goes into the provider rating system.

In one embodiment of the present invention, the myadvisor service maintains a subscriber rating system based on feedback received from providers that have interacted with subscribers. Similar to tracking the ratings of providers, the myadvisor service may also choose to track the users by querying the providers after an introduction. This information may be used to avoid the problem of subscribers who consistently do not enter into a transaction with the recommended provider even after indicating an interest in connecting with the provider. One reason to do so may be that the myadvisor service attracts providers because it offers high quality leads. The providers as much as the users have to benefit from the myadvisor service if the myadvisor service is to be successful. Unhappy users will reduce the number of prospects which will reduce the number of providers which will either increase the work that the myadvisor service has to do to locate the best deal for the user or will result in deals presented to the user that are not very compelling, further reducing the number of users. Similarly, unhappy providers will mean fewer providers which will again reduce the quality of deals for the users. The myadvisor service may use this subscriber rating system in many possible ways, one of which may be to qualify the users to the providers before making an introduction, or to charge the providers different amounts based on the rating or the quality of the lead referred, etc.

According to one embodiment of the present invention, the myadvisor service allows dynamic evolution of buyer-seller ontology. In one embodiment, when a subscriber or a provider is interested in adding a criteria, a product or service or information offer, or a request that is not part of the existing taxonomy of the myadvisor service, they are given one or more of multiple options: the user or provider can communicate with a customer service representative of the myadvisor service either through email, IM, or by filling in a form over the web, or they can create a new leaf in the myadvisor service taxonomy from his internet-connected device (e.g., a desktop). In one embodiment, the myadvisor service may inform relevant users or providers of the availability or need of a product or service. According to various embodiments, when a user or provider creates a new taxonomy leaf, myadvisor service administrators will evaluate it, and if approved all users and providers will see the change and some users and providers will: be notified of the change.

According to one embodiment, anonymous interaction between profiled participants are enabled by the myadvisor service. Since the subscribers (users/potential buyers and providers) have listed profiles, these profiles can be used to promote high value interactions without sacrificing anonymity. For example, a subscriber can request to communicate with other subscribers who also own a Citroen. In one embodiment, the request for communication is indicated to the subscribers who have a Citroen in their profile. The requesting subscriber may indicate how much of his profile he is willing to share with the users who respond to his request, and conversely the subscriber considering to respond may be provided with the ability to ask for other information of the requesting subscriber in order to decide whether to respond.

Having provided an overview of exemplary features which may be provided within an online advisor service, various embodiments and implementations of an online advisor service will now be described with reference to FIGS. 1-11 and the following example including a subscriber named Mike and a service provider named Joe.

Subscriber Mike comes to the myadvisor site, browses through the site, finds category of "possessions", and sub-category of "home". Alternately he could simply search for the keyword "home" and be taken there. If he is coming for the first time, he enters the username and password he wants to use for his future interactions with the myadvisor service. In one embodiment he will use this username and password to access his personal page at the myadvisor site.

Mike wants the myadvisor service to let him know when there are any early weather warnings related to the area in which he lives so he enters the zip code Also, he does not care about offers for his home ("offer to buy") nor about offers for a home in that location ("offer to sell") so he ignores the "offers" tag next to the "home" category. According to one embodiment, if and when there are offers for his home, this tag will change color. At that time, he can continue to ignore it, click on it to see what kinds of offers to buy or sell are being made on his home, or he can specify his provider selection criteria that the myadvisor service can use to select between multiple competing best offers for his home.

Continuing with Mike's current interactions with the myadvisor service, he might next select the "mortgage" sub-category and enter his current mortgage into a standardized template that is presented by the myadvisor service for mortgages: size of mortgage: $360,000, rate: 6%, type: ARM, duration: 5/1, adjusted to: prime plus 0.5% (where the italicized attributes are from the mortgage template provided by the myadvisor service). Since there is an "offers" tag next to mortgages indicating that there are likely to be offers from mortgage providers, he clicks on it and selects from a set of provider selection criteria templates pertinent to mortgages provided by the myadvisor service.

For purposes of the present example, assume that in this case Mike specifies that the provider should have a Better Business Bureau rating of at least 0.6, and amongst all otherwise equal best offers he would prefer to hear from Countrywide, Bank of America, and Washington Mutual. Next, he indicates his reachability from a drop-down menu of reachability templates. In this case, he wants to receive email when the best offer is such that the mortgage payment difference between what he has and the best deal is more than $250 per month. He specifies the address at which he wants to receive email (this information is remembered by the system so that in future interactions he can simply leave the email at which he can be reached as this default or he can change it or he can select from one of the many email addresses he has specified in his interactions with the myadvisor service, etc.). According to one embodiment, if Mike had not specified any reachability information, any best offer would be waiting for him when he logs in next, but he will not be proactively notified of the best offer.

Mike continues his data entry by indicating that his mortgage information is private indicating that the myadvisor service can use the information to get him a better mortgage but should not disclose it to anybody else in a way that Mike can be associated with it. He does not mark his provider selection criteria to be private. There is also an "information bulletin" tag next to mortgages indicating that there are likely to be information bulletins for mortgages. He ignores that and so by default any information bulletin will not be proactively sent to him but will await him at his personal page on the myadvisor service.

Mike then goes back to the "cars" sub-category in the "possessions" category, selects "Volvo" from a drop down menu and fills in a template specifying that his car has 90,000 miles, it is an S70, manufactured in 1998, with no accidents. He does not know if he is the original owner or not so he doesn't bother entering any information there. In one embodiment, the user can enter as much or as little information as he wants—if the myadvisor service needs more information to help catalyze a transaction or provide more information, it may prompt the user for the same, often tantalizing him with the range of possible options. In this particular example, the myadvisor service will let the user know that there are two possible best offers from other users or providers interested in buying his car (the myadisor service can get that information from many independent sources not limited to information entered at the myadvisor site, for example the myadvisor service may get online information from eBay or it may get information from AutoBuyer, etc.): a best offer of $10,000 if he is the original owner and a best offer of $9,200 if he bought the car from a dealer. The user can then give more information and be connected to the appropriate type of buyer, or he can ask for both, or he can connect to the buyer he thinks would be most appropriate for him. Assume for purposes of this example, that Mike does not choose between "offers to buy", "offers to sell", "recalls", "information bulletins" options—options that are pertinent to the "cars" category. Since the user has not specified his interest (or lack of) to the myadvisor service, it will discretely populate the user's personal home page with links to the best offer to buy a car like the user has indicated, to sell such a car, to recalls on such a car, and to information and news clips involving such a car.

Finally, Mike goes to the "medications" sub-category in the "health" category. He enters "Prozac" and "Viagra" under medications, and marks that information private. Based on the fact that he is in the health/medication sub-category, the system presents him with options, "offer to buy", "offer to sell", "side effects", and "breaking news" tags. He selects the "breaking news" tag and specifies his reachability form a drop-down menu like before. In this case he specifies that he wants an SMS to his cell and an IM to his desktop over AIM.

At some independent point in time, assume for purposes of the present example that service provider Joe logs into the myadvisor system. Joe clicks on "Inquire" and types in "mortgages" (he could have also gone to "Possessions", "home", "mortgage" and clicked on "Inquire" there). He fills in the template for mortgages to find out how many people with mortgage amounts of less than $500,000 have an adjustable mortgage with rate greater than 5%. He then browses the list of categories of offers, selects "mortgage", selects the 5/1 ARM option from the drop down list of templates, enters the maximum value of the loan as $500,000, enters 4.5% for the rate he is willing to offer the users, enters $200 for the bounty or referral fee he is willing to offer the myadvisor service, specifies that he wants to be reached on his beeper if someone were to accept his offer, and logs out of the system. In an alternative embodiment, the myadvisor service informs Joe that the minimum bounty for finding a highly qualified prospect for this offer is $100. Joe can choose to agree to this bounty or he can enter a larger amount to improve his chances of being the provider referred to the user out of other providers also offering the same mortgage rate. Many other embodiments are possible, e.g., where the myadvisor service negotiates with Joe, where the myadvisor service gets the providers to bid to make the best offer or to give the highest bounty to the myadvisor service, where Joe enters 2 numbers—one his minimum bounty and the other his maximum bounty and the myadvisor service increases the bounty from Joe up to but no more than the specified maximum bounty to help Joe beat other providers also offering the same best offer, etc. Assume for sake of this example, Joe's payment, credit, and other profile information are already in the system from his last interaction.

Instead of browsing the list of offers, as did Mike, Joe could have gone to category "Possessions", sub-categories "Home" and "Mortgage", selected tag "offer to sell" and entered his offer there. This underscores the buyer-seller duality of the myadvisor service. In one possible embodiment, providers can specify the criteria to select between multiple users who may be interested in their offer. In this example, Joe may choose to specify a user selection criteria that indicates he is not interested in selling mortgages to people in Oakland, Calif. (presumably because they are more prone to default). Such an embodiment demonstrates an additional duality, viz., both buyers and providers can specify the selection criteria for choosing who they want to deal with.

When mentioned above, later in this document, and in the figures, the reference to "contact" as in user or provider contact (as in "contact to Joe" above) is meant to imply the "ability to contact". In one embodiment of the invention, it is indeed the users' or providers' email addresses, telephone numbers, etc., that is made available so that the users or providers can be directly contacted. In another embodiment, the users' or providers' email addresses, telephone numbers, etc., are not disclosed but instead a mutually anonymous communication channel is opened for them. One example of a mutually anonymous communication channel is anonymized, proxied email addresses. In this context, each party sends email to an email address that represents the other party (ies) with whom they are trying to communicate without knowing the actual address to which the email is routed. Another example is where the two (or more) parties are called back at the telephone number they have specified to the myadvisor service without any party knowing the telephone number of any other party. In yet another embodiment, a Wiki page is opened and the parties can write into it, or a blog channel may be initiated, and so on. In this manner, the identity and communication privacy of all parties can be protected until such time as, presumably within the communication channel opened (e.g., call, Wiki, blog) the parties choose to share their identity with the other(s).

FIG. 1 is a block diagram conceptually illustrating a various interactions among an online advisor service, a user and a service provider in accordance with one embodiment of the present invention. While in this simplified example, only a single user 110 and single service provider 120 are shown interacting with the myadvisor service 100, it should be understood that many subscribers and providers may interact with the myadvisor service 100 and directly with each other. According to one embodiment, the hardware components and software modules that implement the myadvisor service are generally provided on or distributed among one or more Internet accessible networked devices, such as one or more servers, web servers, data storage devices, computer systems and the like.

FIG. 2 is a software architecture block diagram conceptually illustrating application-level software components of the online advisor service system in accordance with one embodiment of the present invention.

Figure 3:
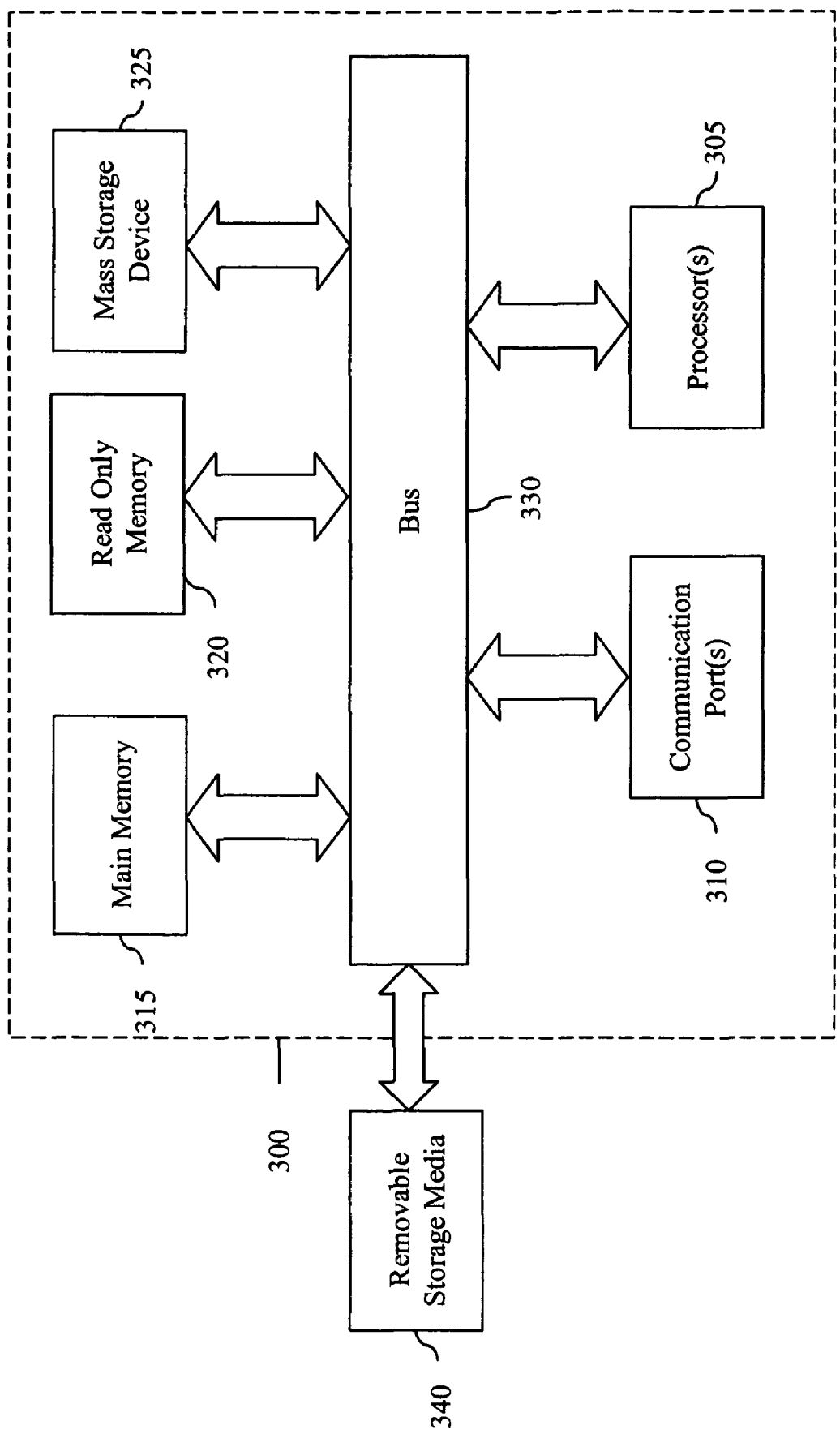
FIG. 3 is an example of a computer system with which embodiments of the present invention may be utilized.

FIG. 3 is an example of a computer system 300 with which embodiments of the present invention may be utilized. The computer system 300 may represent a web server and/or other computer systems involved in the online advisor service system. According to FIG. 3, the computer system 300 includes one or more processors 305, one or more communication ports 310, main memory 315, read only memory 320, mass storage 325, a bus 330, and removable storage media 340.

The processor(s) 305 may be Intel® Itanium® or Itanium 3® processor(s), AMD® Opteron® or Athlon MP® processor(s) or other processors known in the art. Communication port(s) 310 can be any of an RS-232 port for use with a modem based dialup connection, a 10/100 Ethernet port, or a Gigabit port using copper or fiber. Communication port(s) 310 may be chosen depending on the network environment in which the computer system 300 operates, such as the Internet, a Local Area Network (LAN), Wide Area Network (WAN), or any network to which the computer system 300 connects.

Main memory 315 may be Random Access Memory (RAM), or any other dynamic storage device(s) commonly known in the art.

Read only memory 320 may be any static storage device(s) such as Programmable Read. Only Memory (PROM) chips for storing static information such as instructions for processors 305.

Mass storage 325 may be used to store information and instructions. For example, hard disks such as the Adaptec® family of SCSI drives, an optical disc, an array of disks such as RAID, such as the Adaptec family of RAID drives, or any other mass storage devices may be used.

Bus 330 communicatively couples processor(s) 305 with the other memory, storage and communication blocks. Bus 330 may be a PCI/PCI-X or SCSI based system bus depending on the storage devices used.

Optional removable storage media 340 may be any kind of external hard-drives, floppy drives, IOMEGA® Zip Drives, Compact Disc-Read Only Memory (CD-ROM), Compact Disc-Re-Writable (CD-RW), Digital Video Disk-Read Only Memory (DVD-ROM).

Figure 4:
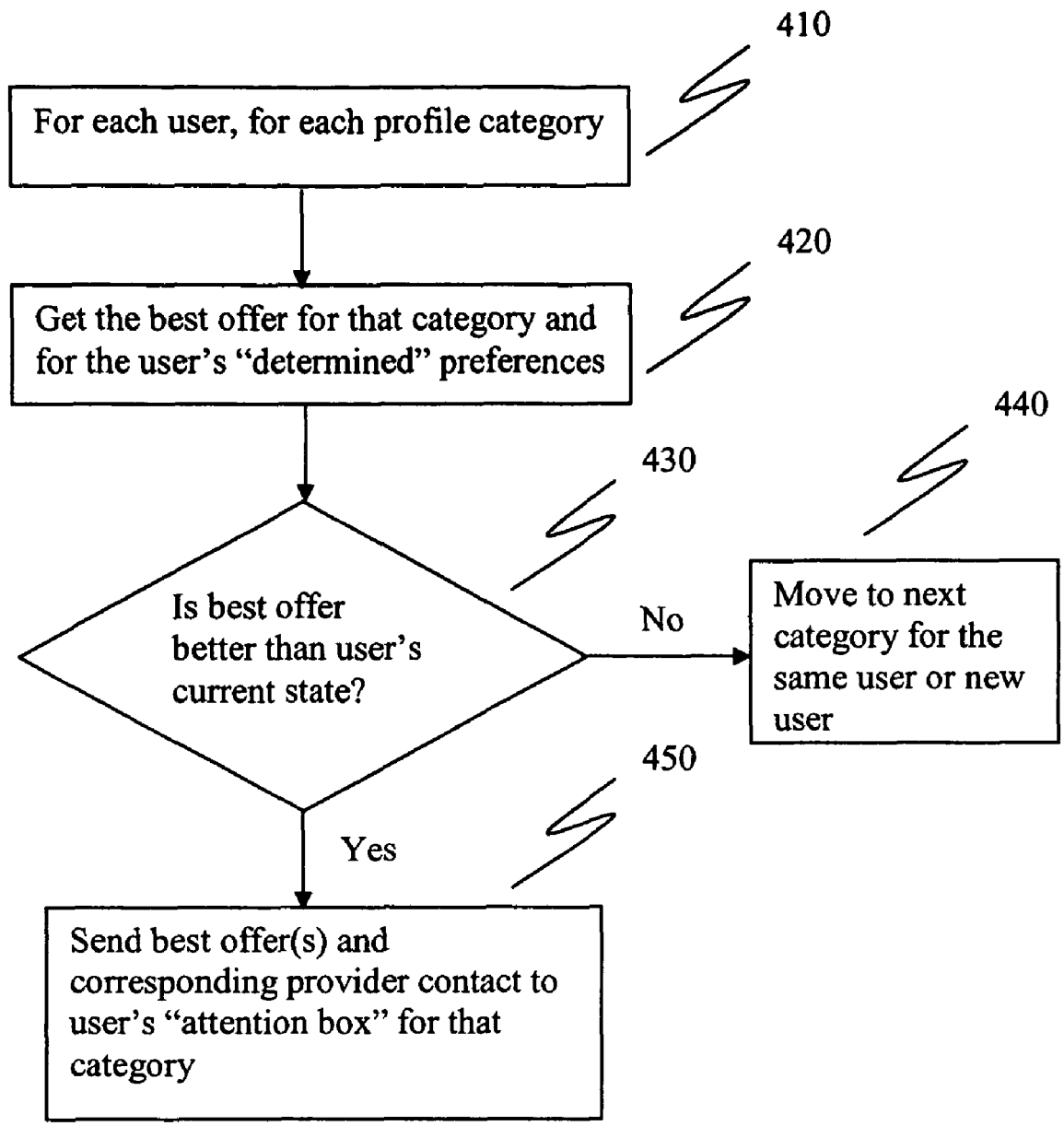
FIG. 4 is a flow diagram illustrating a process of identifying opportunities for subscribers in accordance with an embodiment of the present invention.

FIG. 4 is a flow diagram illustrating a process of identifying opportunities for subscribers in accordance with an embodiment of the present invention. According to this example, the myadvisor service continually compares subscriber profiles with various offers that might be available from providers to look for opportunities to make a connection or enable a transaction.

At block 410, the myadvisor service commences a matching process to identify opportunities in each profile category for each subscriber. At block 420, the myadvisor service identifies the best offer in the current profile category for the current subscriber by applying the subscriber's provider selection criteria for the current profile category to the available offers. As indicated above, a subscriber's provider selection criteria may be used by the myadvisor service to select between multiple competing best offers. For example, the myadvisor service may have one or more provider selection criteria templates associated with each profile category. Using one of the provider selection criteria templates, the subscriber may set up various selection and filtering criteria, such as preferred service providers, BBB ratings, membership in certain trade groups, public vs. private company, years in operation, minimum provider rating score, market capitalization, name recognition, number of employees, social responsibility measure, diversity metric, and other category-specific information.

At decision block 430, the myadvisor service evaluates the best offer determined in block 420 against the subscriber's current state to determine if the best offer is better than the subscriber's current state in the particular profile category. If the best offer is better than the subscriber's current state, then processing continues with block 450; otherwise control branches to block 440.

At block 440, the matching process continues to the next category for the current user. If all categories for the current user have been evaluated, then the matching process continues by moving to the next subscriber until all subscribers have been processed.

At block 450, the best offer(s) and corresponding provider contact information is sent to the subscriber's attention box for the current category. For example, in one embodiment, best offers determined to be better than the subscriber's current state are posted to the subscriber's home page within the myadvisor service web site.

In the context of the example of subscriber Mike and service provider Joe, the myadvisor service checks Mike's current mortgage with those offered by Joe and others. It finds that the best offer (in this case Joe's) has a lower interest rate (4.5%) than what Mike is currently paying (6%) and the best offer results in a savings of more than $250 per month. Since the provider met Mike's provider selection criteria (user's "determined" preferences), Joe's best offer and a contact to Joe is sent to Mike's "attention box" for the category/sub-category of possessions/home/mortgage. Since the offer also met Mike's reachability criteria, Joe's best offer and a contact to Joe is also sent by email to Mike.

The myadvisor service also checks Mike's profile under the "Health" category, finds "Prozac" in Mike's "medications" sub-category. When the myadvisor service checks its information sources for Prozac, it finds that there is a "breaking news" story regarding the links between Prozac and high blood pressure. The myadvisor service finds from Mike's reachability for breaking news on Prozac that Mike wants the headline of the story sent to him over IM and SMS. It also finds the cheapest seller of Prozac. But, the seller needs to know if the Prozac strength is 50 mg or 100 mg, because the prices for 50 mg tablets of Prozac is different than those for 100 mg tablets of Prozac.

As discussed further below, since Mike's profile does not have sufficient information for myadvisor to select the best offer to sell Prozac to Mike, a request for additional information may be sent to Mike to allow the myadvisor service to better determine the match between the seller and Mike. In a situation where one seller had a better price for 50 mg tablet and another seller had a better price for 100 mg tablets, the myadvisor service may prompt Mike for dosage information to allow the service to distinguish between the two sellers or both these best offers, each the best for different attributes unspecified in Mike's profile, may be sent to Mike. For purposes of the present example, assume a request for additional information is sent to Mike's attention box, and therefore on Mike's home page there will be a request for additional information on a "Profile fine tune" section and also at the Health/medications category of Mike's page.

The next time Mike logs into the myadvisor service, Mike will be prompted to select between 50 mg and 100 mg, which will go into his profile and in response Mike's page will be updated with the appropriate best offer to sell Prozac to Mike and the appropriate seller link. In an alternative embodiment seller links and seller best prices for both 50 mg and 100 mg strengths may be presented to Mike on his home page. Then, Mike may refine his profile if he desires to have the myadvisor service filter offers appropriately in the future or provide more relevant information to Mike. In other embodiments, in addition to or instead of requesting information from subscribers after an actual need for further information is determined, the myadvisor service may proactively evaluate subscriber profiles to determine their sufficiency for purposes of selecting between competing providers.

Figure 5:
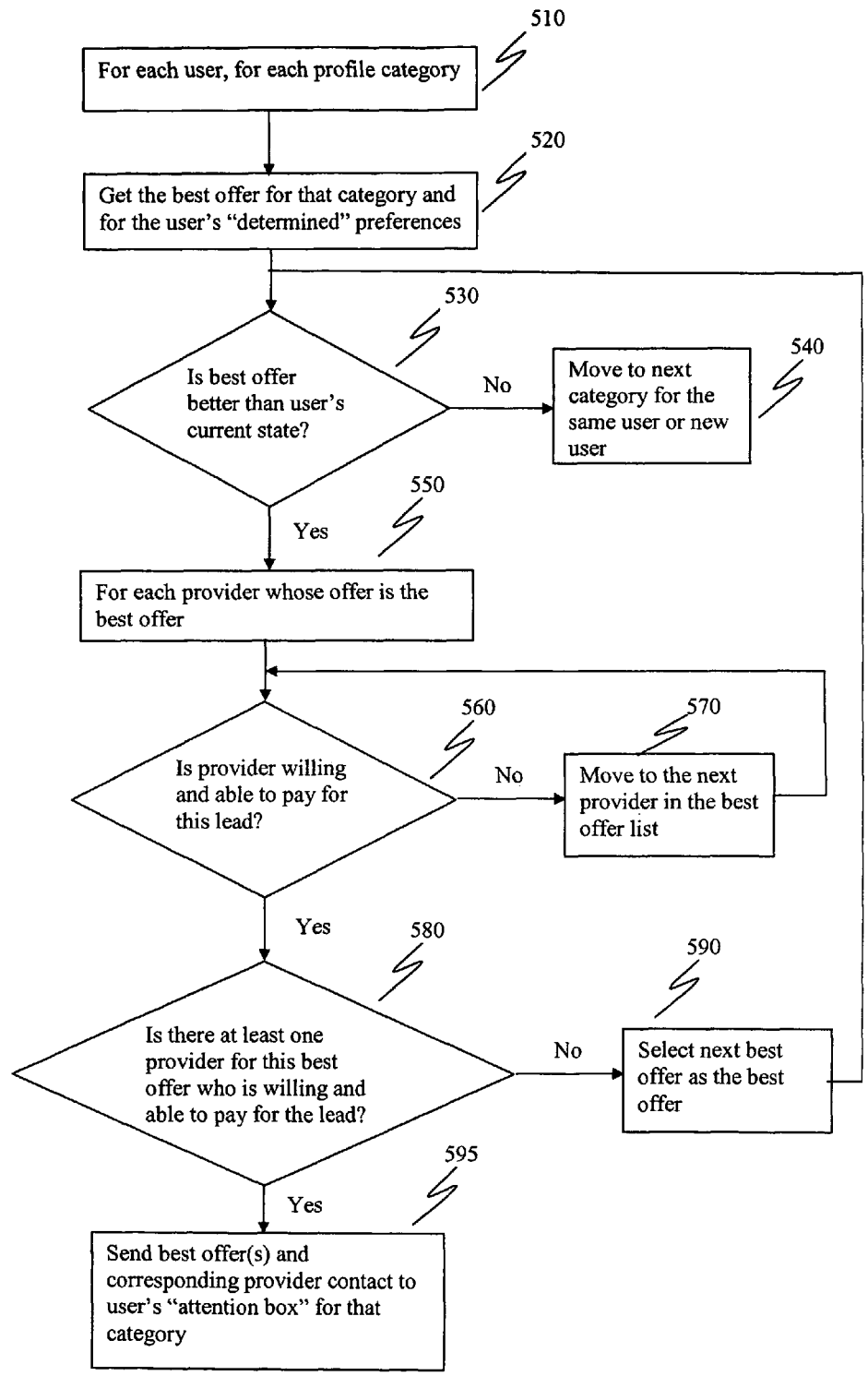
FIG. 5 is a flow diagram illustrating a process of identifying opportunities for subscribers in accordance with an alternative embodiment of the present invention.

FIG. 5 is a flow diagram illustrating a process of identifying opportunities for subscribers in accordance with an alternative embodiment of the present invention. In this example, after best offers have been determined to be better than the current subscriber's current state, the myadvisor service verifies the ability and willingness of the providers represented in the list of best offers to pay for the lead.

At block 550, the myadvisor service commences a check for each provider having an offer in the list of best offers that have been determined to both meet the subscriber's provider selection criteria (block 520) and be better than the subscriber's current state (block 530).

At block 560, a determination is made regarding the current provider's willingness and ability to pay for the lead. In one embodiment the provider's willingness and ability to pay for the lead is part of the provider's profile. As mentioned earlier, if this profile information is not disclosed by the provider, the myadvisor service interacts with the provider to get that information. In another embodiment as soon as the provider indicates an interest to submit an offer to sell this information is required (and evaluated, such as the provider's creditworthiness, etc.). If the current provider is either unwilling or unable to pay for the lead, then processing continues with block 570; otherwise processing continues with decision block 580.

At block 570, having determined the current provider is either unwilling or unable to pay for the lead, the myadvisor service moves to the next provider in the best offer list until a provider willing to pay for the lead is identified or until all providers having an offer in the best offer list have been evaluated.

At decision block 580, a determination is made whether there is at least one provider for this best offer who is willing and able to pay for the lead. If there is at least one such provider, then processing continues with block 595; otherwise processing branches to block 590.

At block 590, no providers having an offer in the current best offer list are both willing and able to pay for the lead. Consequently, the next best offer is selected as the best offer for further evaluation and processing continues with decision block 530.

At block 595, the best offer(s) in the best offer list associated with a provider both willing and able to pay for the lead are sent to the subscriber's attention box for the current category along with contact information for the corresponding provider(s).

Returning again to the example of subscriber Mike and service provider Joe, after it is determined that Joe's mortgage offer is better than Mike's current state and meets his provider selection criteria, the myadvisor service checks to see if service provider Joe is willing to pay the pre-specified bounty or referral fee to the myadvisor service (as mentioned earlier alternative embodiments are possible to determine the payment due to the myadvisor service and to determine the provider to be presented to Mike) and that Joe's creditworthiness allows it. If not, then Joe is not presented to the user, either proactively or passively on the user's personal page, and instead the next best provider is checked for willingness and ability to pay for the connection to Mike.

In one embodiment Joe's account is debited the determined bounty and that money is put in escrow. If Mike subsequently clicks on Joe's contact to connect with him through the myadvisor service, then the referral fee amount will be transferred from the escrow account to the myadvisor service. In an alternative implementation, Joe's account is not debited until Mike elects to connect with Joe. Joe's account is debited (and the myadvisor account) is credited with the bounty amount at that time. In yet another possible embodiment, there may be 2 or more different bounty amounts, one that Joe pays simply to be presented to Mike, and another when Mike actually connects with Joe. Various other mechanisms in which the myadvisor service gets revenue for directing and/or connecting leads to providers are possible. For example, the myadvisor service may be paid a commission equal to a percentage or fraction of a percentage on any transaction completed between the subscriber and provider resulting from the lead.

Figure 6:
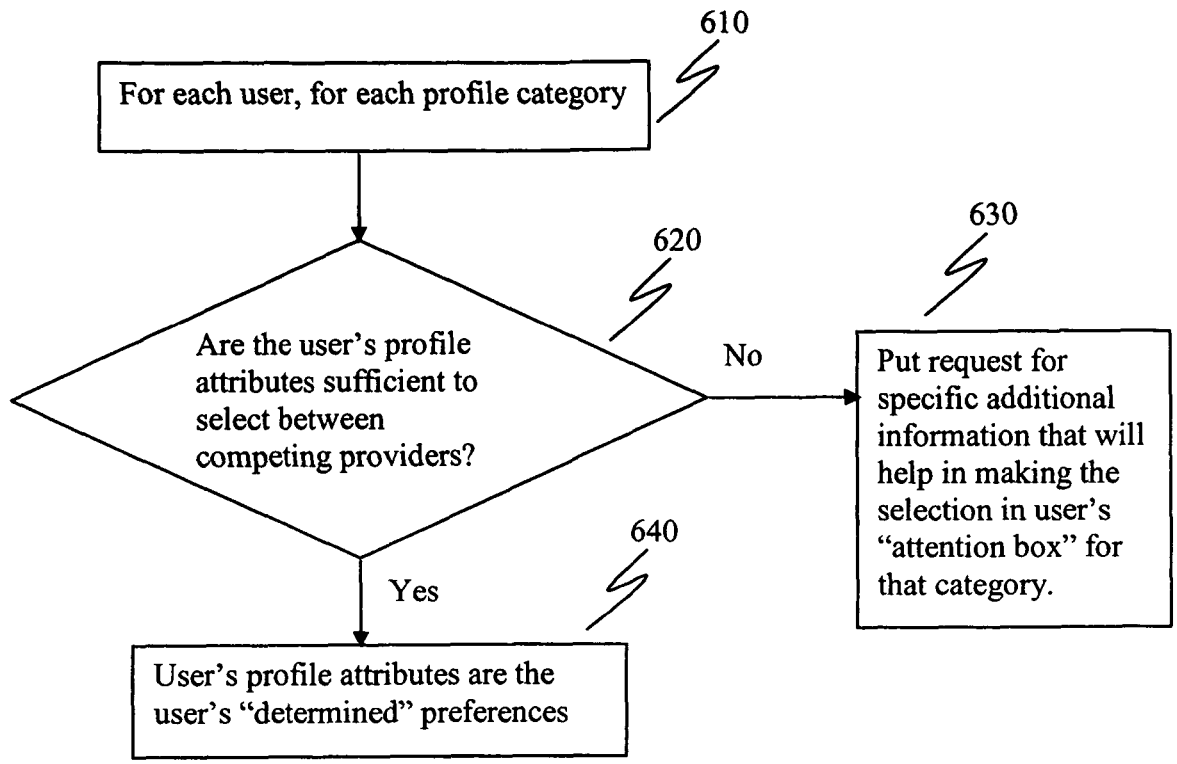
FIG. 6 is a flow diagram illustrating a process of determining sufficiency of subscriber profiles for purposes of selecting between competing providers in accordance with an embodiment of the present invention.

FIG. 6 is a flow diagram illustrating a process of determining sufficiency of subscriber profiles for purposes of selecting between competing providers in accordance with an embodiment of the present invention.

In one possible embodiment, the myadvisor service uses the following algorithm to test for completeness of information and to determine whether it should prompt the user for additional information or selection criteria.

According to one embodiment, categories and sub-categories are structured in a hierarchy and every category/sub-category has its own unique attribute hierarchy. So for example, for mortgages the hierarchy could be possessions/home/own/mortgage/fixed, that is to say within the "possessions" category, there is a "home" sub-category (other possibilities are "health", etc.). Within the "home" sub-category there is an "own" sub-category (other possibilities are "rent", "lease", etc.). Within the "own" sub-category there is the "mortgage" sub-category (other possibilities are "paid up", etc.). Within the "mortgage" sub-category there is the "fixed" sub-category (other possibilities are "adjustable", etc.). And the "fixed" sub-category has multiple attributes that define the fixed mortgage parameters, for example, "loan amount", "period", etc.

If an offer has the same sub-categories and attributes as the user's profile, then a simple match against the user's current state can be made based on the matching rules for this type of offer (e.g., lower mortgage rate is better). However, there may be multiple offers that cannot be simply compared to each other. For example one offer may specify that the attribute of "points" has value 1.5. And another may specify 0 points. Now, if the 0 points offer has a lower rate than the 1.5 points offer, life is simple. However, it is possible that the 0 points offer has a higher rate than the 1.5 points offer. In this case, the myadvisor service cannot select the better of these offers—which is better depends on the user's ability and willingness to pay points to get a lower mortgage rate, which in turn depends on the number of years before the user expects to refinance or move, and such other information that the myadvisor service may or may not have. In this case, the myadvisor service can either present multiple offers to the user, essentially the lowest mortgage rate for 0 points, 1.5 points, etc (and if the lowest mortgage rate for 1.5 points is higher than the lowest mortgage rate for 0 points then it does not need to present the lowest rate for 1 points; the myadvisor service has such a model for comparing different offers for each type of offer) and let the user decide, or the myadvisor service can choose to ask the user to specify his offer selection criteria (e.g., interested only in 0 point offers) and then present to the user only the best offer that matches the user's selection criteria. Similarly, the myadvisor service may need to know the location of the house at issue and the user may not have specified that in his profile. In this case, the myadvisor service can ask for location information from the user (by indicating it in the "Profile fine tune" section of the user's home page and also at the Home/location sub-category of the user's home page). The myadvisor service can optionally, when available, present to the user the lowest mortgage for all locations, thus prompting the user to enter his information to see if he can get to that low rate.

As indicated below, the myadvisor service can also prompt the user with "best practice" criteria. So, for example, when it is asking the user to specify his preference, the myadvisor service can indicate to the user that going for 0 points is the recommended approach. Similarly, the user can select to query the myadvisor service for the criteria selected by other users with some profile that is of interest to the user. In general, each offer and each profile category/sub-category in the myadvisor service may have specific rules for how to deal with insufficient information, best practices, etc.

At block 610, the myadvisor service commences a profile verification process to identify potential need for specific additional information in the subscriber's profile to facilitate selection among multiple competing providers by the myadvisor service.

At decision block 620, the myadvisor service evaluates the current subscriber's profile to determine its sufficiency to select among competing providers. If the subscriber's profile attributes are determined to be sufficient, then processing continues with block 640; otherwise control flow branches to block 630.

At block 630, a request is delivered to the subscriber for additional information that will help the myadvisor service select among competing providers. For example, the myadvisor service may indicate the desired information by providing a list of options to select from on the "Profile fine tune" section of the user's home page. In one embodiment, the myadvisor service may prompt the user with "best practice" criteria. So, for example, in the context of a mortgage, the myadvisor service may indicate to the user that a 0 point loan is the recommended approach when it is asking him to specify his preference. Similarly, the subscriber can select to query the myadvisor service for the criteria selected by other users with some profile that is of interest to the user. Each offer and each profile category/sub-category in the myadvisor service may have specific rules for how to deal with insufficient information, best practices, etc.

At block 640, the subscriber's profile attributes have been determined to be sufficient to allow the myadvisor service to adequately distinguish among competing providers. Consequently, the subscriber's provider selection criteria for the current category need not be refined.

Returning once again to the example of subscriber Mike, the myadvisor service checks Mike's profile under the "Health" category, finds "Prozac" in Mike's "medications" sub-category. The myadvisor service also finds the cheapest seller of Prozac. But, the seller needs to know if the Prozac strength is 50 mg or 100 mg, because the prices for 50 mg tablets of Prozac is different than those for 100 mg tablets of Prozac. Consequently, it is determined that Mike's profile does not have sufficient information for myadvisor to select the best offer to sell Prozac to Mike. Hence in Mike's attention box, and therefore on Mike's home page there will be a request for additional information on a "Profile fine tune" section and also at the Health/medications category of Mike's page. Mike will be asked to select between 50 mg and 100 mg, which will go into his profile and in response Mike's page will be updated with the appropriate best offer to sell Prozac to Mike and the appropriate seller link. In an alternative embodiment seller links and seller best prices for both 50 mg and 100 mg strengths may be presented to Mike on his home page.

Figure 7:
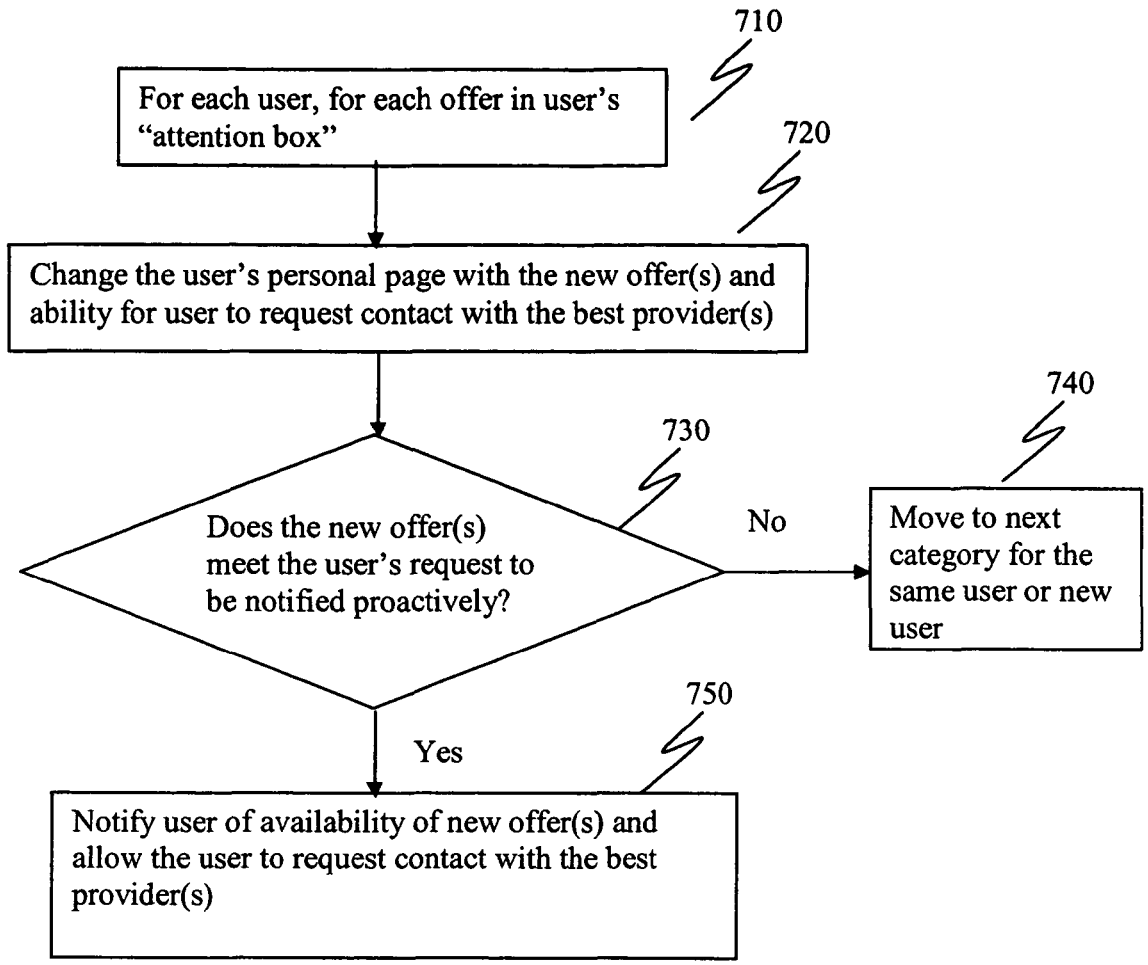
FIG. 7 is a flow diagram illustrating a process of notifying users of new offers in accordance with an embodiment of the present invention.
Figure 8:
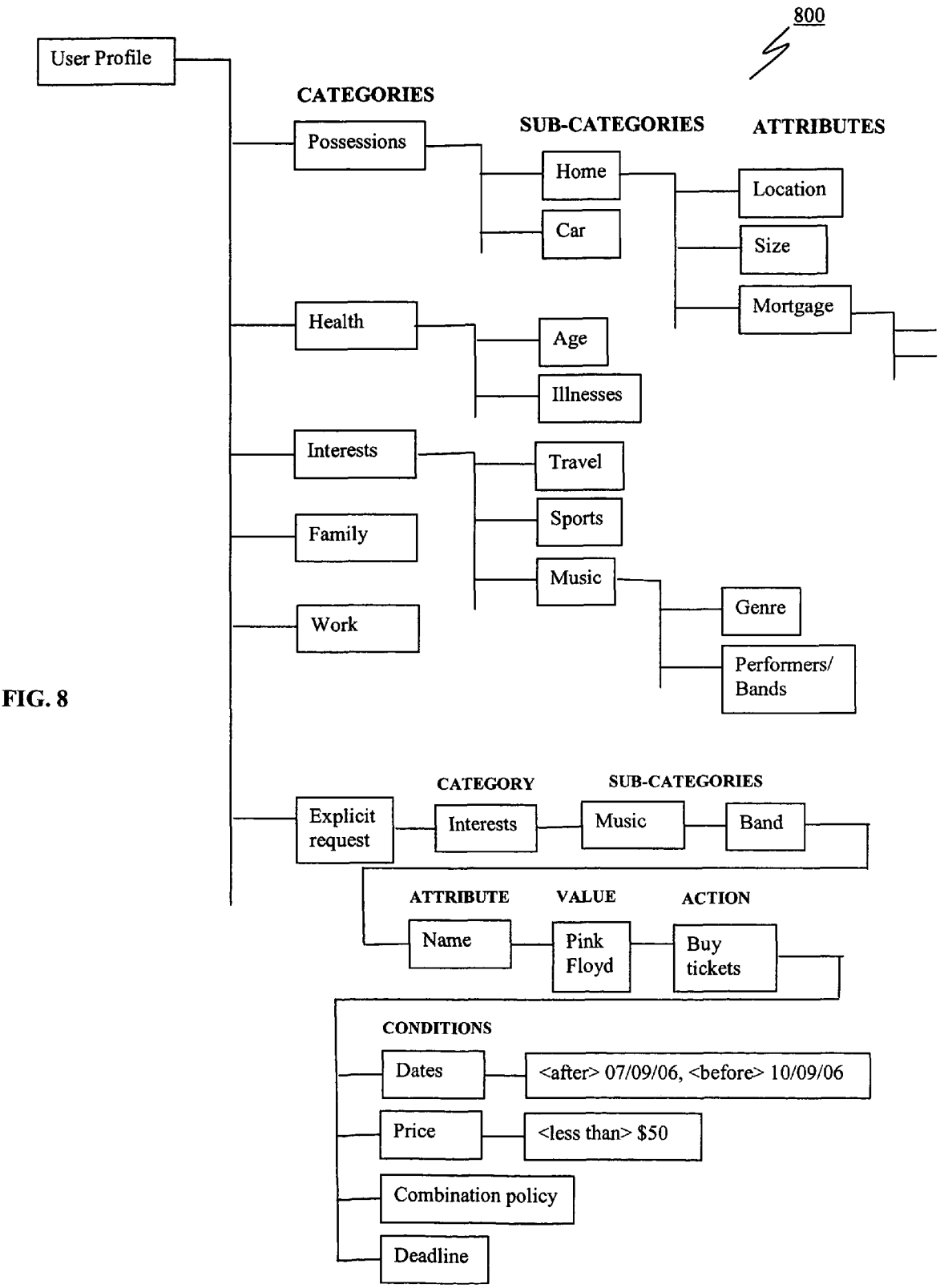
FIG. 8 is a conceptual illustration of a data structure representing a subscriber profile in accordance with an embodiment of the present invention.
Figure 9A:
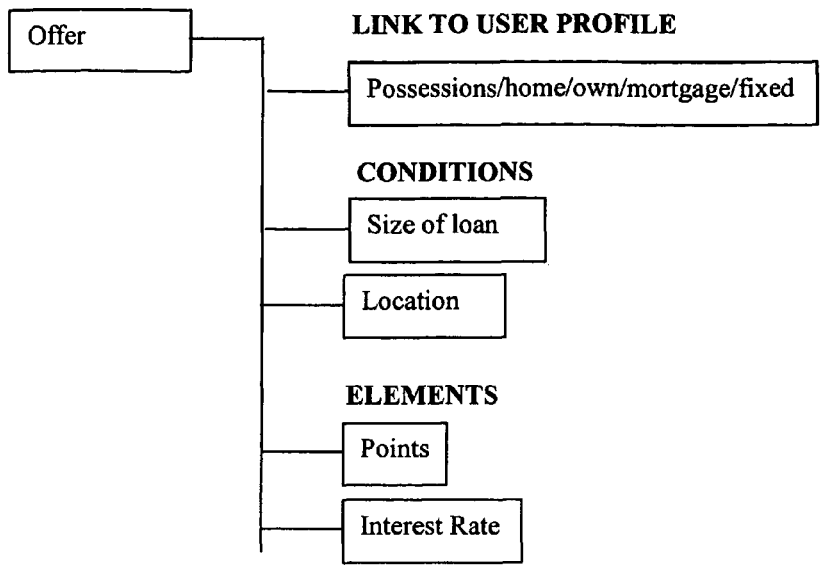
FIG. 9 conceptually illustrates data structures representing an offer, a provider profile and selection criteria in accordance with an embodiment of the present invention.
Figure 9B:
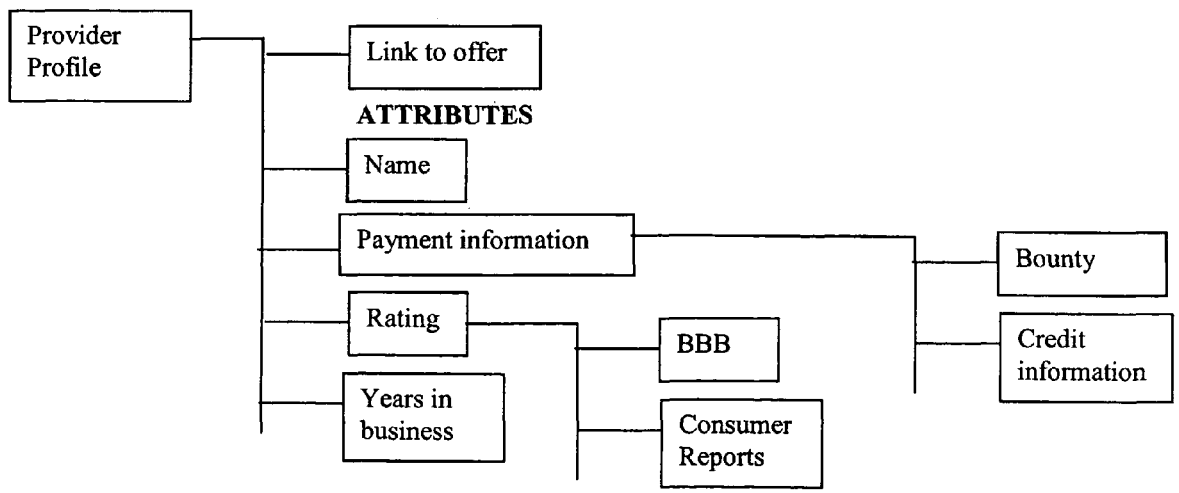
Figure 9C:
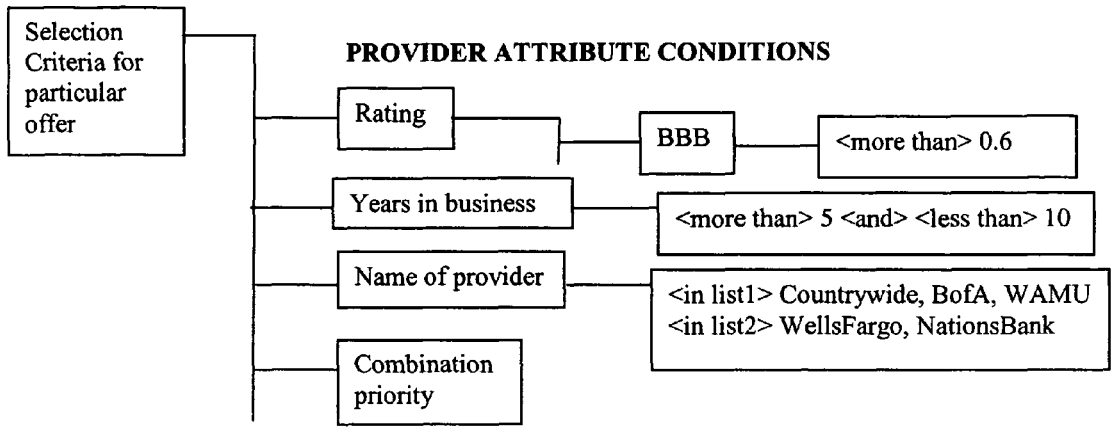
Figure 9D:
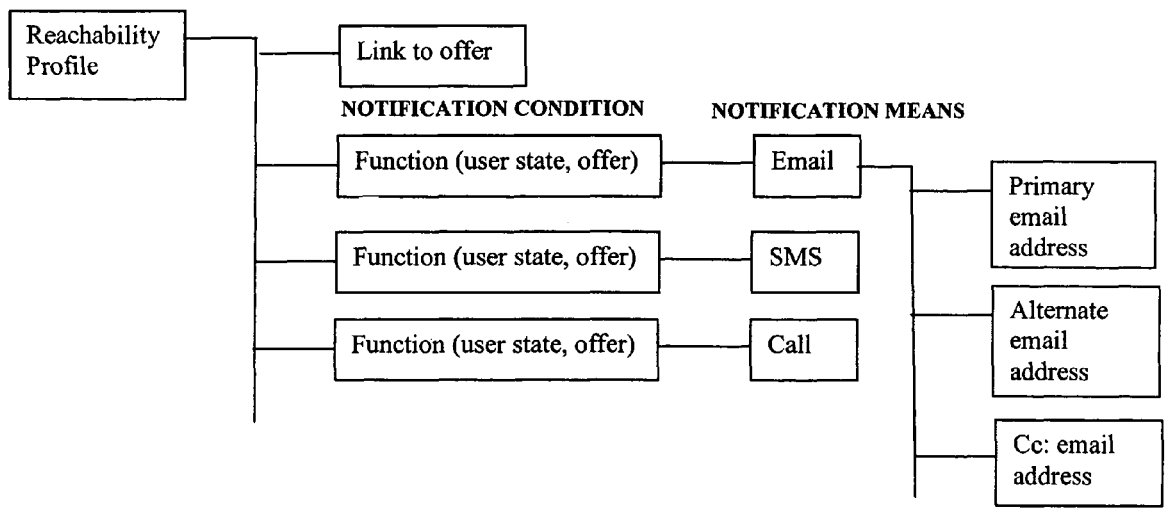

FIG. 7 is a flow diagram illustrating a process of notifying users of new offers in accordance with an embodiment of the present invention. In the present example, the myadvisor service continually checks the "attention, box" of each subscriber and determines the appropriate notification methodology.

At block 710, the myadvisor service initiates checking of each subscriber's attention box. At block 720, the myadvisor service updates the subscriber's personal home page on the myadvisor web site to include the new offer(s). The myadvisor service may also include contact information for providers that may be associated with the new offer(s). According to one embodiment, the subscriber's personal home page on the myadvisor service web site is updated with the new offer and provider contact information (could be a link to the provider's web site or a telephone number to call, etc.).

At decision block 730, the myadvisor service determines if the new offer(s) meet the subscriber's proactive notification criteria. If so, processing continues with block 750; otherwise processing continues with block 740.

At block 740, no proactive notification by the myadvisor service is required for the particular type of new offer(s). Therefore, the myadvisor service continues to check attention boxes by moving to the next category for the same subscriber or by moving to the next subscriber until all subscribers and categories have been checked.

At block 750, the subscriber is notified of the availability of the new offer(s) in accordance with his reachability profile (in general references to "offer" also cover offers to buy, offers to sell, news, information, etc., that may be of interest to subscribers). Through the proactive notification in his reachability profile, the subscriber may request contact with the provider(s) associated with the new offer(s).

In our example with subscriber Mike, Mike's personal page is updated with the mortgage offer from Joe and with a link to Joe's web site. Since Mike had specified his reachability for this type of offer to be notified through email, an email is also sent to Mike with a link to his home page on the myadvisor service, the best offer from Joe, and a link to Joe's web site.

Figure 10:
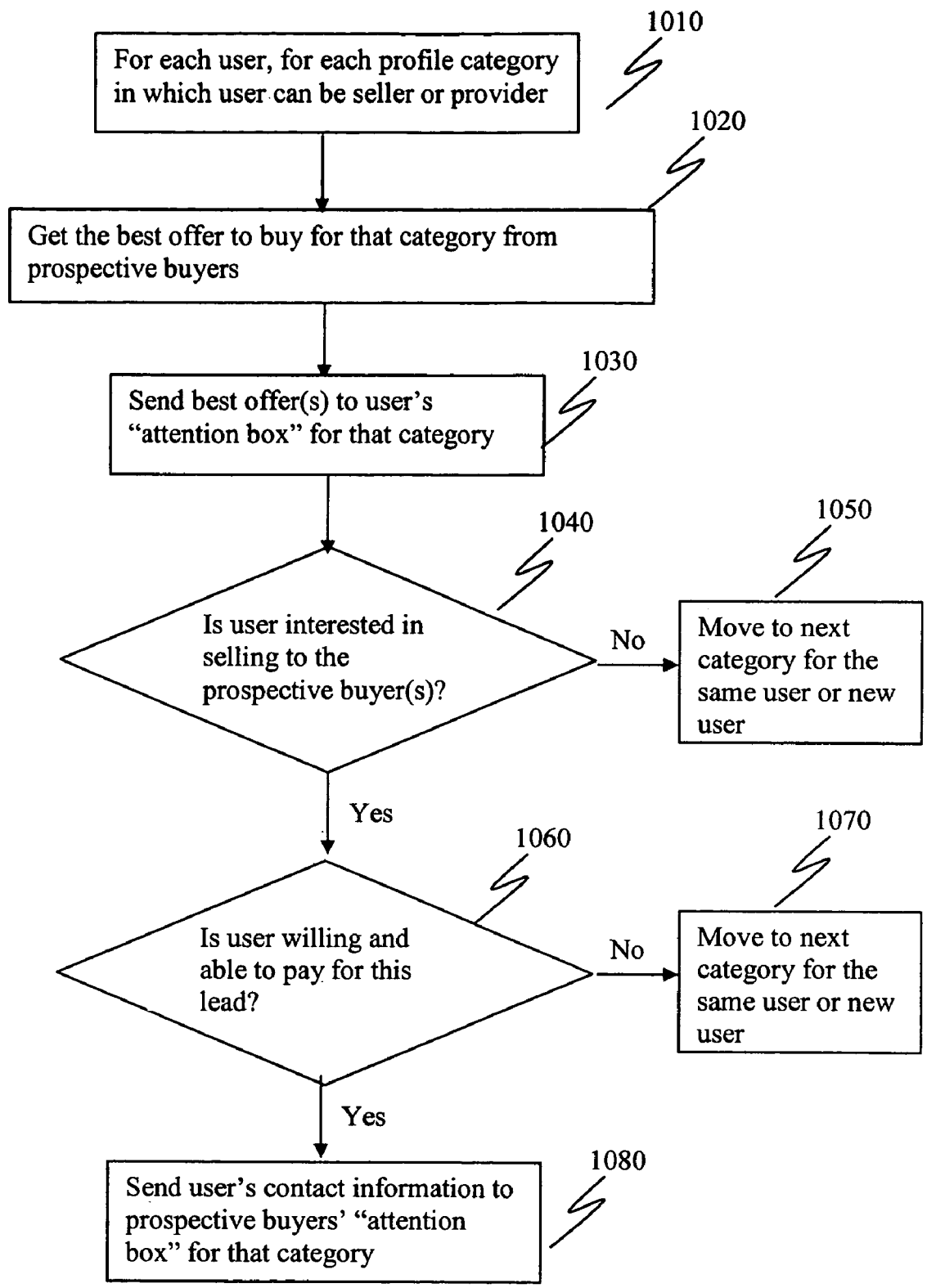
FIG. 10 is a flow diagram illustrating a process for directing leads to subscribers acting as providers in accordance with an embodiment of the present invention.

FIG. 10 is a flow diagram illustrating a process for directing leads to subscribers acting as providers in accordance with an embodiment of the present invention. At block 1010, the myadvisor service commences a matching process to identify opportunities in each profile category for each subscriber in their provider capacity.

At block 1020, the myadvisor service identifies the best offer to buy the corresponding product or service from the profiles and implicit and explicit requests of other users and providers in the system, and from other potential buyers outside the myadvisor user base. According to one embodiment, the myadvisor service applies the subscriber's user selection criteria for the current profile category to appropriately filter the potential buyers.

At block 1030, the best offer(s) are sent to the subscriber's attention box for the current category.

At decision block 1040, a determination is made regarding the subscriber's willingness and interest in selling to the identified prospective buyer(s). According to one embodiment, the myadvisor service applies the subscriber's user selection criteria for the current profile category to programmatically determine whether the potential buyer(s) meet the subscriber-specified selection criteria. According to another embodiment, the subscriber indicates interest by manually selecting the relevant potential buyer link on the subscriber's personal home page on the myadvisor web site and making a "connect" request. In any event, if a determination is made that the subscriber is interested in selling to the identified prospective buyer(s), then processing continues with decision block 1060; otherwise processing continues with block 1050.

At block 1050, the myadvisor service continues to the next category for the same subscriber or continues with a new subscriber if all the categories for the current subscriber have been processed.

At decision block 1060, a determination is made whether the subscriber is willing and able to pay for this lead. In one embodiment the subscriber's willingness and ability to pay for the lead is part of the subscriber's profile. As mentioned earlier, if this profile information is not disclosed by the subscriber, the myadvisor service interacts with the subscriber to get that information. In another embodiment as soon as a subscriber indicates an interest to submit an offer to sell, this information is required (and evaluated, such as the subscriber's creditworthiness, etc.). If the subscriber is either unwilling or unable to pay for the lead, then processing continues with block 1070; otherwise processing continues with block 1080.

At block 1070, having determined the current subscriber is either unwilling or unable to pay for the lead, the myadvisor service moves to the next category for the same subscriber or if this is the last category to the next subscriber.

At block 1080, the subscriber's contact information is sent to the prospective buyers' attention box for the current category.

Finally, concluding the example with subscriber Mike, the myadvisor service checks the Possessions/Cars category of Mike's profile. It finds recall notices and other information related to Mike's 1998 Volvo S70 and posts it along with any relevant service provider links on Mike's web page under the appropriate headings: information bulletins, recalls, and offers to sell. It also finds some users and service providers (dealerships) who are interested to buy a 1998 Volvo S70. As described above, the myadvisor service finds the highest offer to buy the car and sends the best offer (to buy) to Mike's attention box and hence to his personal web page. In this case, there is information missing from Mike's profile. Similar to what Joe did, Mike needs to agree to, negotiate, or otherwise select the bounty he is willing to pay the myadvisor service to sell his car. And, similar to the interaction with Joe, Mike enters his payment and credit information. All else being equal Mike would prefer to sell his car to an individual rather than a dealer, so he specifies this in the user selection criteria option presented to him under the "offer to sell" tag. As mentioned earlier this user selection criteria is the dual of the provider selection criteria. The myadvisor service updates Mike's home page with the best offer to buy and the contact to the interested buyer(s) who made the best offer as determined by a number of factors including (but not limited to) the myadvisor service based on Mike's criteria, the myadvisor service's selection mechanisms (that may take into account the bounty offered, as mentioned earlier), and the criteria of the prospective buyer. In this case Mike has become the provider or seller.

Figure 11:
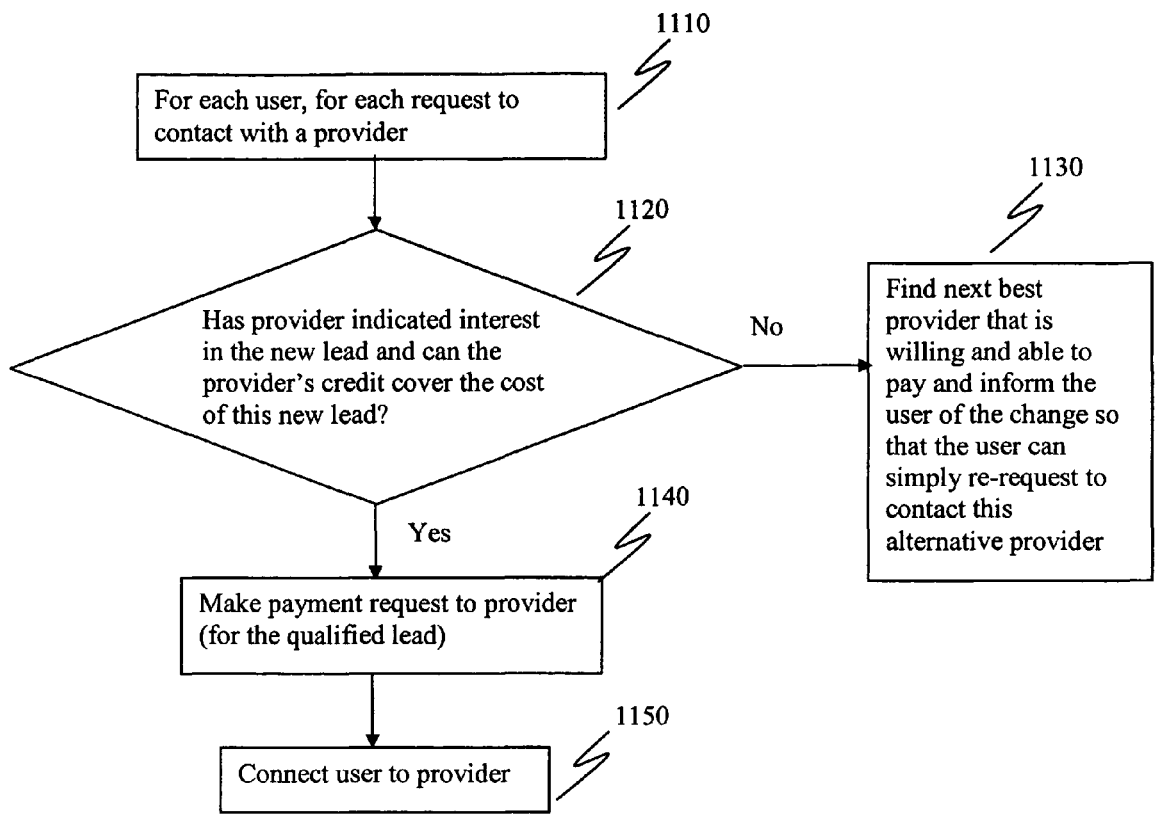
FIG. 11 is a flow diagram illustrating a process for directing leads to providers in accordance with an embodiment of the present invention.

FIG. 11 is a flow diagram illustrating a process for directing leads to providers in accordance with an embodiment of the present invention.

At block 1110, the myadvisor service commences a check for each subscriber having one or more outstanding "connect" requests or requests to contact with a provider.

At decision block 1120, a determination is made regarding the provider's willingness and ability to pay for the lead. In one embodiment the provider's willingness and ability to pay for the lead is part of the provider's profile. As mentioned earlier, if this profile information is not disclosed by the provider, the myadvisor service interacts with the provider to get that information. In another embodiment as soon as a provider indicates an interest to submit an offer to sell, this information is required (and evaluated, such as the provider's creditworthiness, etc.). If the provider is either unwilling or unable to pay for the lead, then processing continues with block 1130; otherwise processing continues with decision block 1140.

At block 1140, a payment request is made to the provider for the qualified lead.

At block 1150, the subscriber is connected to the provider.

While embodiments of the invention have been illustrated and described, it will be clear that the invention is not limited to these embodiments only. Numerous modifications, changes, variations, substitutions, and equivalents will be apparent to those skilled in the art, without departing from the spirit and scope of the invention, as described in the claims.

What is claimed is:

1. A method comprising
    a computer system of a personal advisor service, the computer system having a processor, the computer system receiving information indicative of one or more needs of a subscriber of the personal advisor service;
    the personal advisor service evaluating a subscriber profile associated with the subscriber to generate one or both of an inferred need and a continuing need, wherein the inferred need and the continuing need are each different from the one or more needs;
    the personal advisor service proactively generating, using the processor, information regarding one or more offers for the subscriber by identifying and selecting among potential transactions, potential transaction providers, or transactable information determined to address or alleviate the one or both of the inferred need and the continuing need; and
    the personal advisor service causing the one or more offers to be communicated to the subscriber in accordance with a reachability profile established by the subscriber.

2. The method of claim 1, further comprising:
    refining criteria to distinguish among the potential transactions or the potential transaction providers by interacting with the subscriber; and
    wherein the one or more offers are based at least in part upon application of the refined criteria to the potential transactions or the potential transaction providers.

3. The method of claim 1, wherein the personal advisor service recommends appropriate selection criteria based on selection criteria employed by other subscribers of the personal advisor service.

4. The method of claim 1, wherein a bidding or auction process is applied to select among competing providers of the potential transaction providers.

5. The method of claim 1, wherein the personal advisor service provides the subscriber or the provider with the ability to query statistics regarding other subscribers of the personal advisor service without compromising privacy of the other subscribers or providers.

6. The method of claim 1, wherein the personal advisor service provides the subscriber with the ability to query ratings of transaction providers maintained by the personal advisor service without compromising privacy of the transaction providers, and wherein the ratings are obtained from other current or past subscribers of the personal advisor service.

7. The method of claim 1, wherein the personal advisor service supports dynamic evolution of a taxonomy within which subscribers and transaction providers are categorized by adding a criteria, product, service or request responsive to a request from the subscriber.

8. The method of claim 1, wherein the personal advisor service maintains profiles containing private information regarding a plurality of subscribers of the personal advisor service, the method further comprising enabling anonymous interaction among providers and consumers of the plurality of subscribers responsive to connection requests by the providers or consumers and based on commonality of attributes in the profiles of the providers or consumers.

9. The method of claim 1, wherein the personal advisor service maintains profiles for a plurality of subscribers of the personal advisor service, preferences of the plurality of subscribers and decisions made by the plurality of subscribers, the method further comprising receiving information from a subscriber of the plurality of subscribers indicating which aspects of the subscriber's profile, preferences, and decisions, if any, the subscriber is willing to allow the personal advisor service to share and with whom, how and under what conditions.

10. The method of claim 1, wherein the personal advisor service applies bidding and auctioning mechanisms to select among potential transaction providers to be presented to the subscriber.

11. The method of claim 1, wherein the personal advisor service maintains a provider rating system.

12. The method of claim 1, wherein the personal advisor service maintains a subscriber rating system.

13. The method of claim 1, wherein the computer system of the personal advisor service includes software running on an end-user's machine, on an internet service, or on the end-user's machine and the internet service.

14. The method of claim 1, wherein the personal advisor service further provides one or more templates to the subscriber that allow the subscriber to enter personal information and create a subscriber profile, and wherein the method further comprises querying information about other subscribers in a generalized and anonymous manner.

15. The method of claim 1, wherein some or all of the subscriber profile is obtained from one or more of the subscriber's blog and the subscriber's personal computer.

16. The method of claim 1, wherein the personal advisor service has access to a subscriber profile with information about the subscriber and wherein the subscriber profile is used to enhance on-line interactions of a subscriber based on selective information from the subscriber's profile or from the profile of similar users.

17. The method of claim 1, wherein the subscriber and provider are duals of each other, whereby all restrictions, capabilities, ratings, profiles, privacy, and rights of a provider are also applied to the subscriber and vice versa.

18. The method of claim 1, wherein the subscriber is one of a plurality of subscribers and the subscriber profile is one of a plurality of subscriber profiles each associated with different subscribers and the method further comprises:

generating an anonymous aggregate summary of subscriber needs from the plurality of subscriber profiles in response to a query from a provider;

publishing the summary of subscriber needs to enable the provider to generate a bid for the one or more of the plurality of subscriber's business;

receiving a new offer from the provider; and presenting the new offer to a subset of the plurality of subscribers based on a request from the provider.

19. The method of claim 1, wherein the potential transaction providers self-register with the personal advisor service or information about the potential transaction providers is provided by the subscriber.

* * * * *